(12) United States Patent
Elia et al.

(10) Patent No.: US 9,849,070 B2
(45) Date of Patent: Dec. 26, 2017

(54) POSTPYLORIC FEEDING DEVICE AND METHODS FOR USING THEREOF

(75) Inventors: Liron Elia, Kiryat-Ata (IL); Gavriel J. Iddan, Haifa (IL); Nir Lilach, Kfar Yehoshua (IL)

(73) Assignee: ART Healthcare Ltd., Natania (IL)

( * ) Notice: Subject to any disclaimer, the term of this patent is extended or adjusted under 35 U.S.C. 154(b) by 258 days.

(21) Appl. No.: 14/342,382

(22) PCT Filed: Aug. 29, 2012

(86) PCT No.: PCT/IB2012/054442
§ 371 (c)(1),
(2), (4) Date: Mar. 2, 2014

(87) PCT Pub. No.: WO2013/030775
PCT Pub. Date: Mar. 7, 2013

(65) Prior Publication Data
US 2014/0330076 A1  Nov. 6, 2014

Related U.S. Application Data

(60) Provisional application No. 61/575,730, filed on Aug. 29, 2011.

(51) Int. Cl.
*A61B 1/00* (2006.01)
*A61J 15/00* (2006.01)
(Continued)

(52) U.S. Cl.
CPC ...... *A61J 15/0007* (2013.01); *A61B 1/00154* (2013.01); *A61B 1/015* (2013.01);
(Continued)

(58) Field of Classification Search
USPC ......... 600/106–107, 139–142, 146–153, 156
See application file for complete search history.

(56) References Cited

U.S. PATENT DOCUMENTS 4,769,014 A * 9/1988 Russo ............... A61M 25/01
604/270
4,801,297 A * 1/1989 Mueller ............ A61M 25/0045
604/247
(Continued)

FOREIGN PATENT DOCUMENTS

EP       1557192       7/2005
WO   WO 2009/006335   1/2009
(Continued)

OTHER PUBLICATIONS

International Preliminary Report on Patentability dated Mar. 13, 2014 From the International Bureau of WIPO Re. Application No. PCT/IB2012/054442.
(Continued)

*Primary Examiner* — Matthew J Kasztejna

(57) ABSTRACT

A feeding tube device for postpyloric feeding that comprises a bendable feeding tube having a proximal end, a central portion and, and a distal end and a delivery lumen therealong for conducting a digestible substance therethrough, an imaging unit having an image sensor mounted on a tip of the distal end to image an imaging space thereinfront, and a tilting mechanism for tilting the distal end in relation to the central portion. The distal end has at least one lateral tilt and feeding opening therealong for delivering the digestible substance therethrough, the at least one lateral tilt and feeding opening are laid out so that when the tilting mechanism tilts the distal end the at least one lateral tilt and feeding opening narrows.

9 Claims, 26 Drawing Sheets

(51) Int. Cl.
*A61B 1/015* (2006.01)
*A61B 1/273* (2006.01)
(52) U.S. Cl.
CPC .......... *A61B 1/2736* (2013.01); *A61J 15/0026* (2013.01); *A61J 15/0088* (2015.05); *A61J 15/0049* (2013.01); *A61J 15/0069* (2013.01)

(56) References Cited

U.S. PATENT DOCUMENTS

| | | | |
|---|---|---|---|
| 4,911,148 | A | 3/1990 | Sosnowski et al. |
| 5,179,934 | A | 1/1993 | Nagayoshi et al. |
| 5,665,064 | A | 9/1997 | Bodicky et al. |
| 5,860,953 | A * | 1/1999 | Snoke ................ A61B 1/00105 604/95.04 |
| 6,322,495 | B1 * | 11/2001 | Snow ................ A61B 1/00082 600/114 |
| 7,344,494 | B2 * | 3/2008 | Hoeg ................ A61B 1/00183 600/170 |
| 8,361,041 | B2 * | 1/2013 | Fang ...................... A61B 1/042 600/109 |
| 8,678,999 | B2 * | 3/2014 | Isaacson ................ A61B 1/303 600/104 |
| 9,060,922 | B2 * | 6/2015 | Nieman ............. A61B 1/00052 |
| 9,526,674 | B2 * | 12/2016 | Heyns .................. A61M 39/08 |
| 2005/0020974 | A1 * | 1/2005 | Noriega ............ A61M 25/0054 604/95.04 |
| 2005/0197534 | A1 | 9/2005 | Barbato et al. |
| 2006/0116552 | A1 | 6/2006 | Noguchi et al. |
| 2007/0015968 | A1 * | 1/2007 | Shelnutt ............. A61B 1/00156 600/156 |
| 2007/0203393 | A1 * | 8/2007 | Stefanchik ........ A61B 1/00073 600/106 |
| 2008/0228066 | A1 * | 9/2008 | Waitzman ................ A61B 5/06 600/424 |
| 2009/0275825 | A1 * | 11/2009 | Thomas ............. A61B 5/14539 600/424 |
| 2009/0318798 | A1 * | 12/2009 | Singh ..................... A61B 1/012 600/424 |
| 2010/0280316 | A1 * | 11/2010 | Dietz ....................... A61B 8/12 600/109 |
| 2012/0116160 | A1 * | 5/2012 | Nieman ............. A61B 1/00052 600/114 |
| 2015/0025311 | A1 | 1/2015 | Kadan et al. |
| 2017/0135560 | A1 | 5/2017 | Elia et al. |

FOREIGN PATENT DOCUMENTS

| | | |
|---|---|---|
| WO | WO 2009/115914 | 9/2009 |
| WO | WO 2010/118256 | 10/2010 |
| WO | WO 2013/030775 | 3/2013 |
| WO | WO 2017/085724 | 5/2017 |

OTHER PUBLICATIONS

Supplementary European Search Report and the European Search Opinion dated Jun. 29, 2015 From the European Patent Office Re. Application No. 12827550.0.
Communication Pursuant to Rule 164(1) EPC and the Supplementary Partial European Search Report dated Mar. 10, 2015 From the European Patent Office Re. Application No. 12827550.0.
International Search Report and the Written Opinion dated Jan. 14, 2013 From the International Searching Authority Re. Application No. PCT/IB2012/054442.
European Search Report and the European Search Opinion dated Nov. 8, 2016 From the European Patent Office Re. Application No. 16182381.0. (7 Pages).
International Search Report and the Written Opinion dated Feb. 3, 2017 From the International Searching Authority Re. Application No. PCT/IL2016/051240. (17 Pages).

* cited by examiner

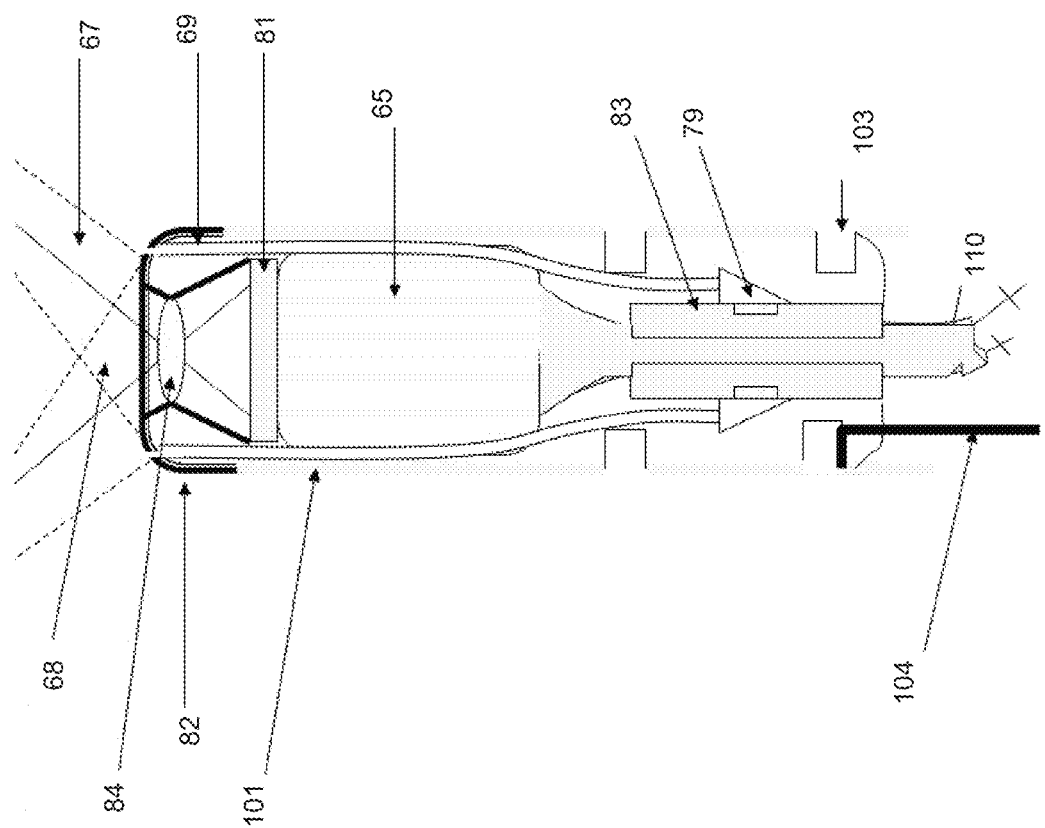

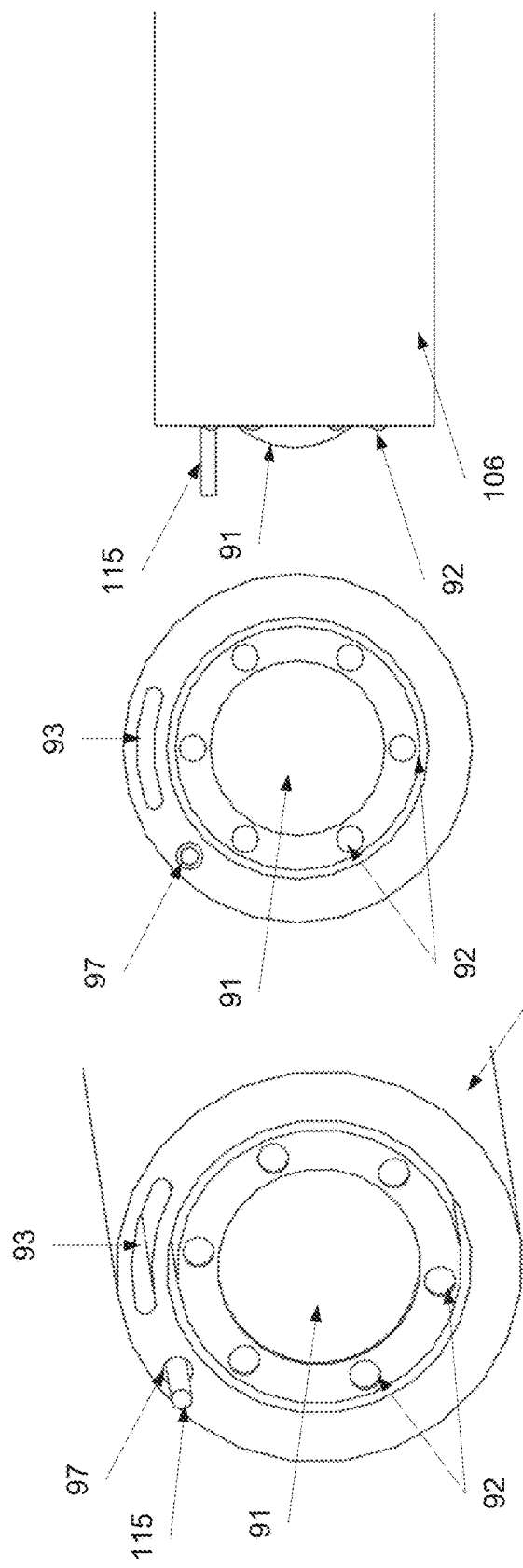

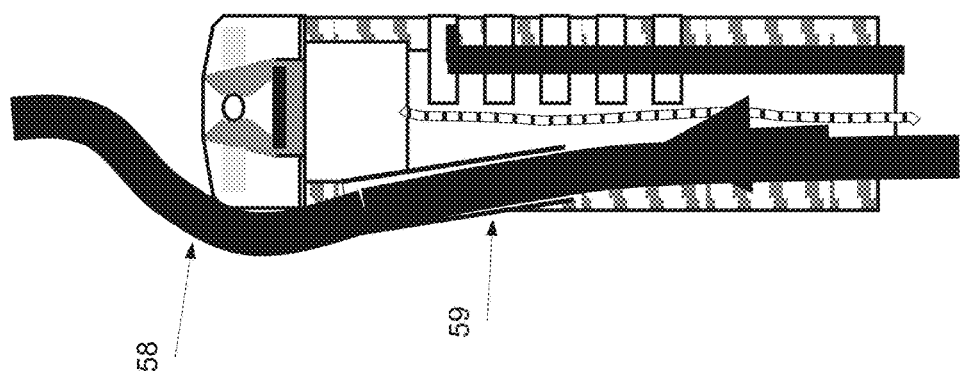
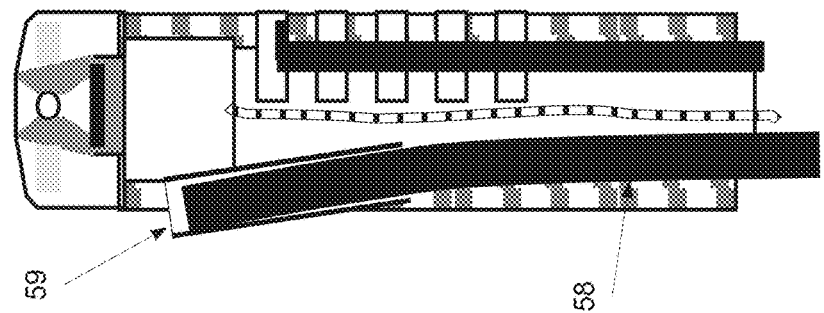

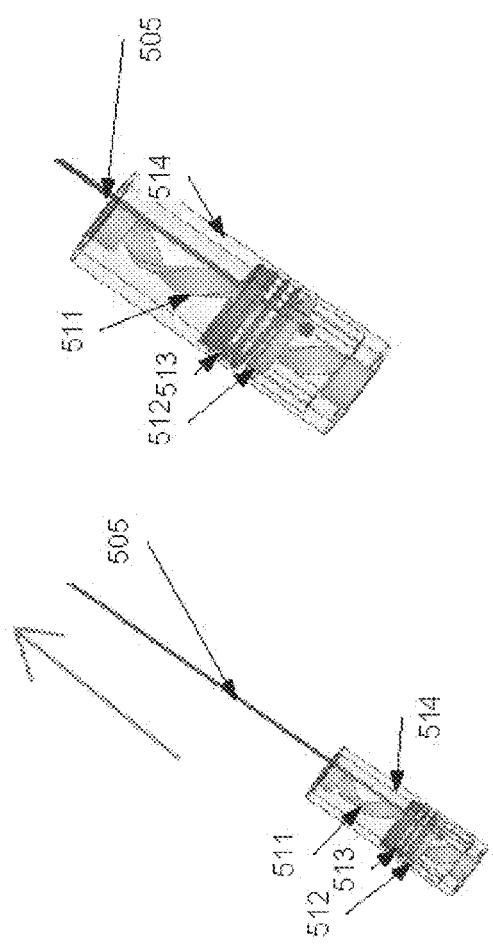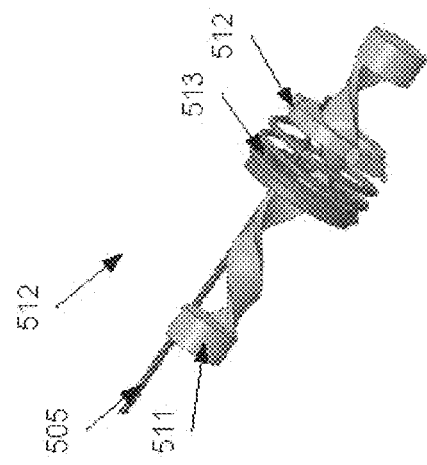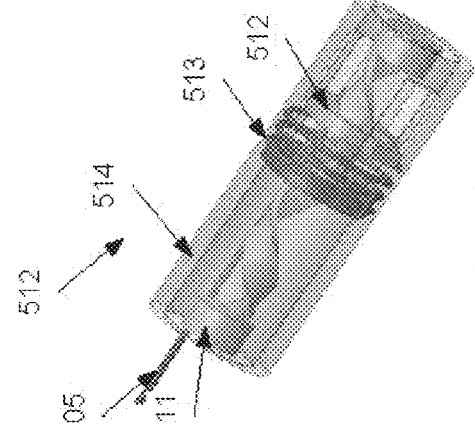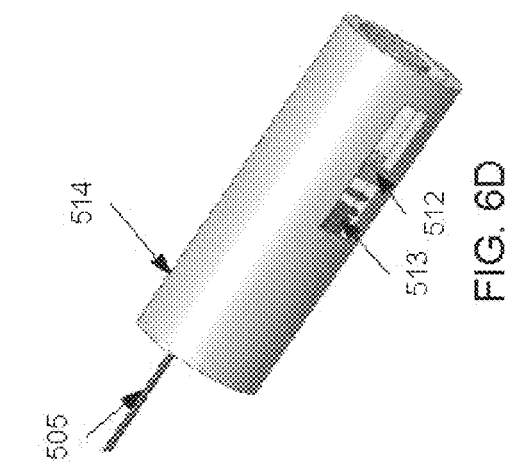
FIG. 6B
FIG. 6C
FIG. 6D
FIG. 6E
FIG. 6F

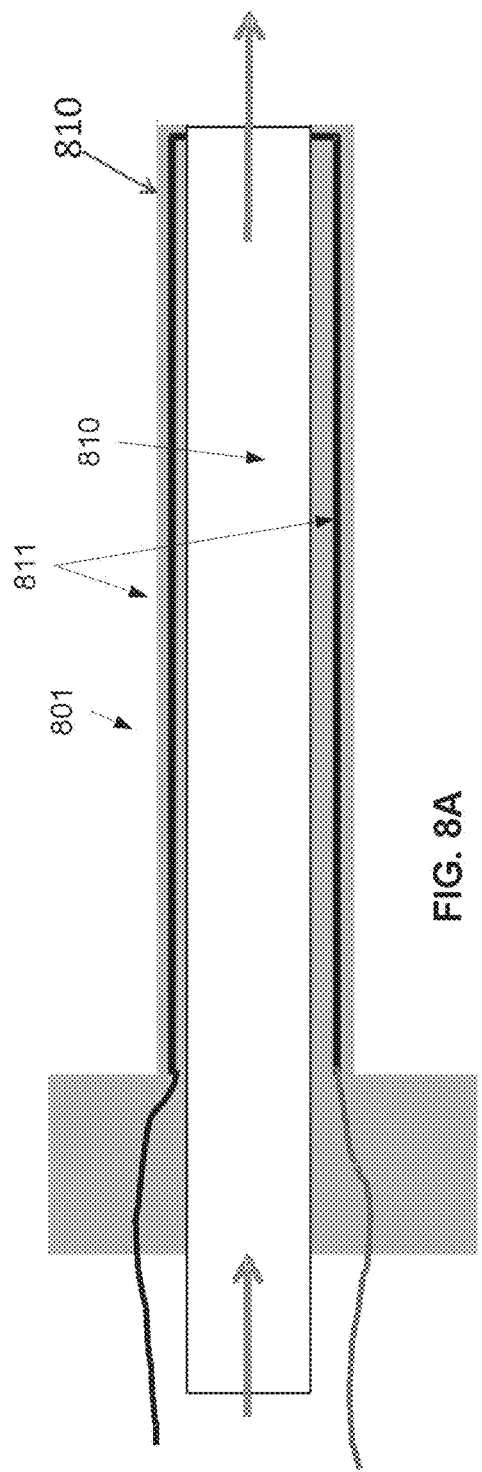
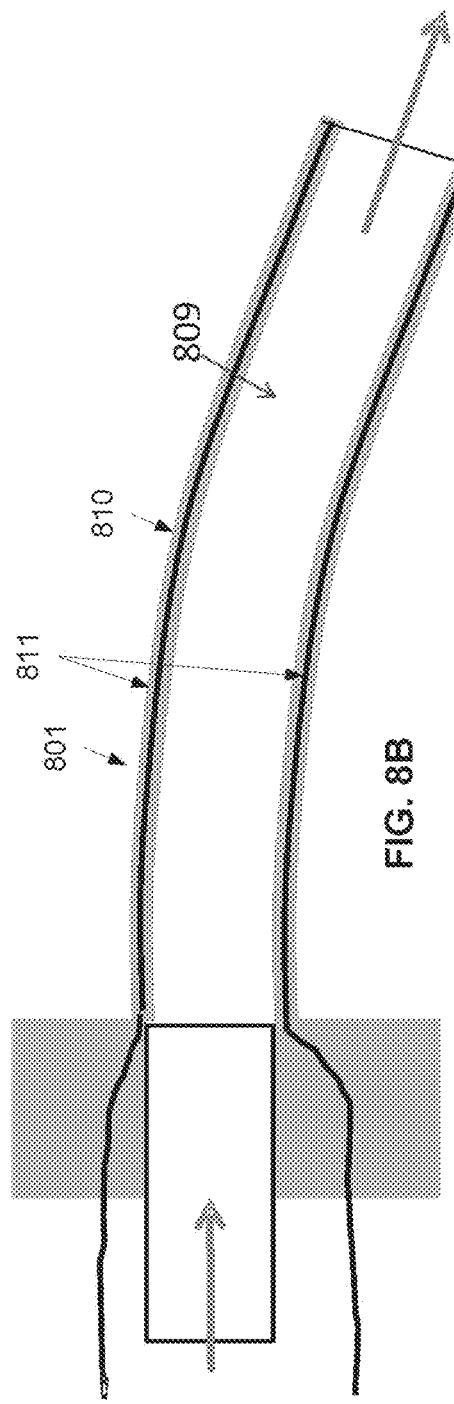
FIG. 8A
FIG. 8B

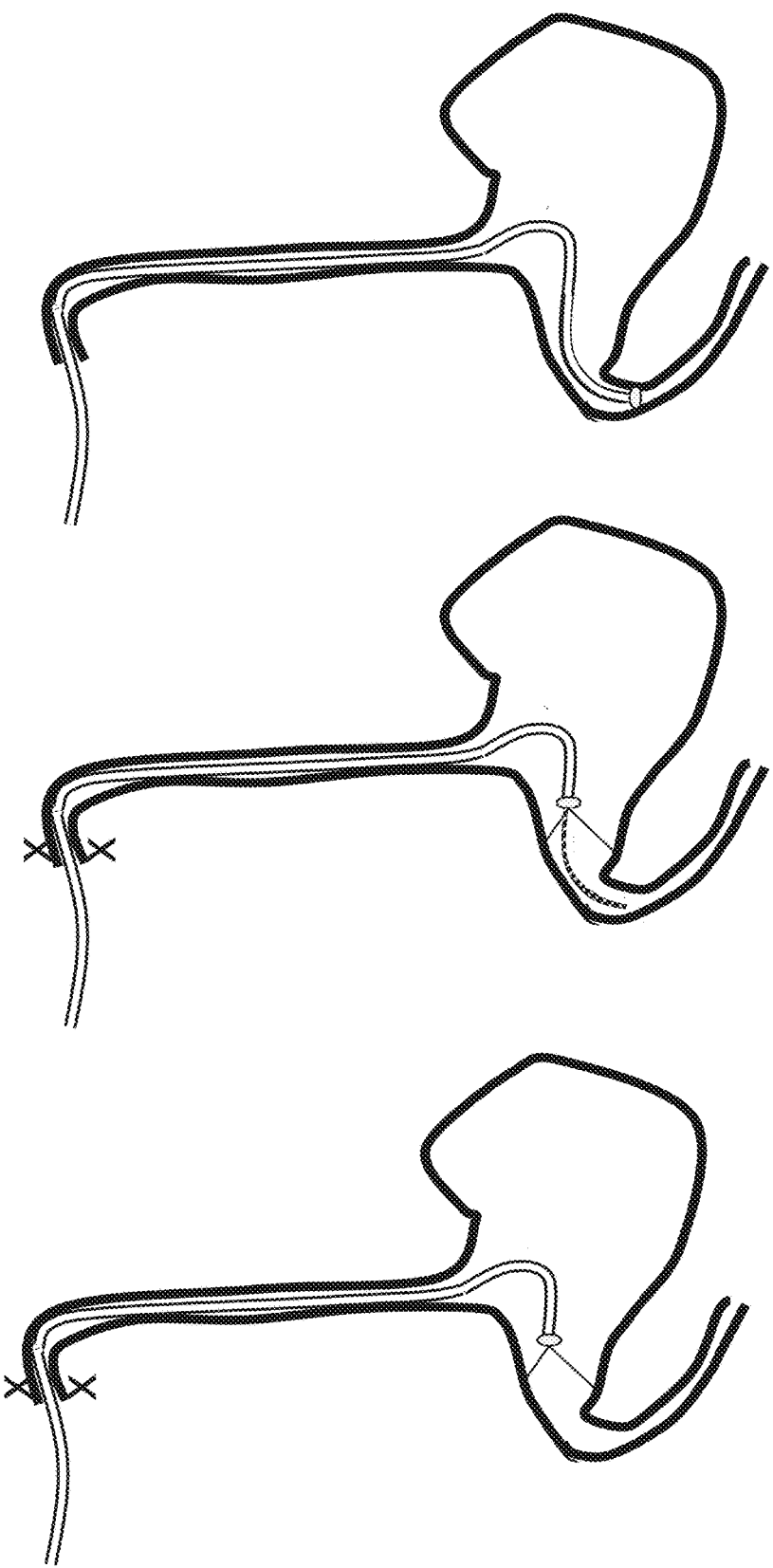

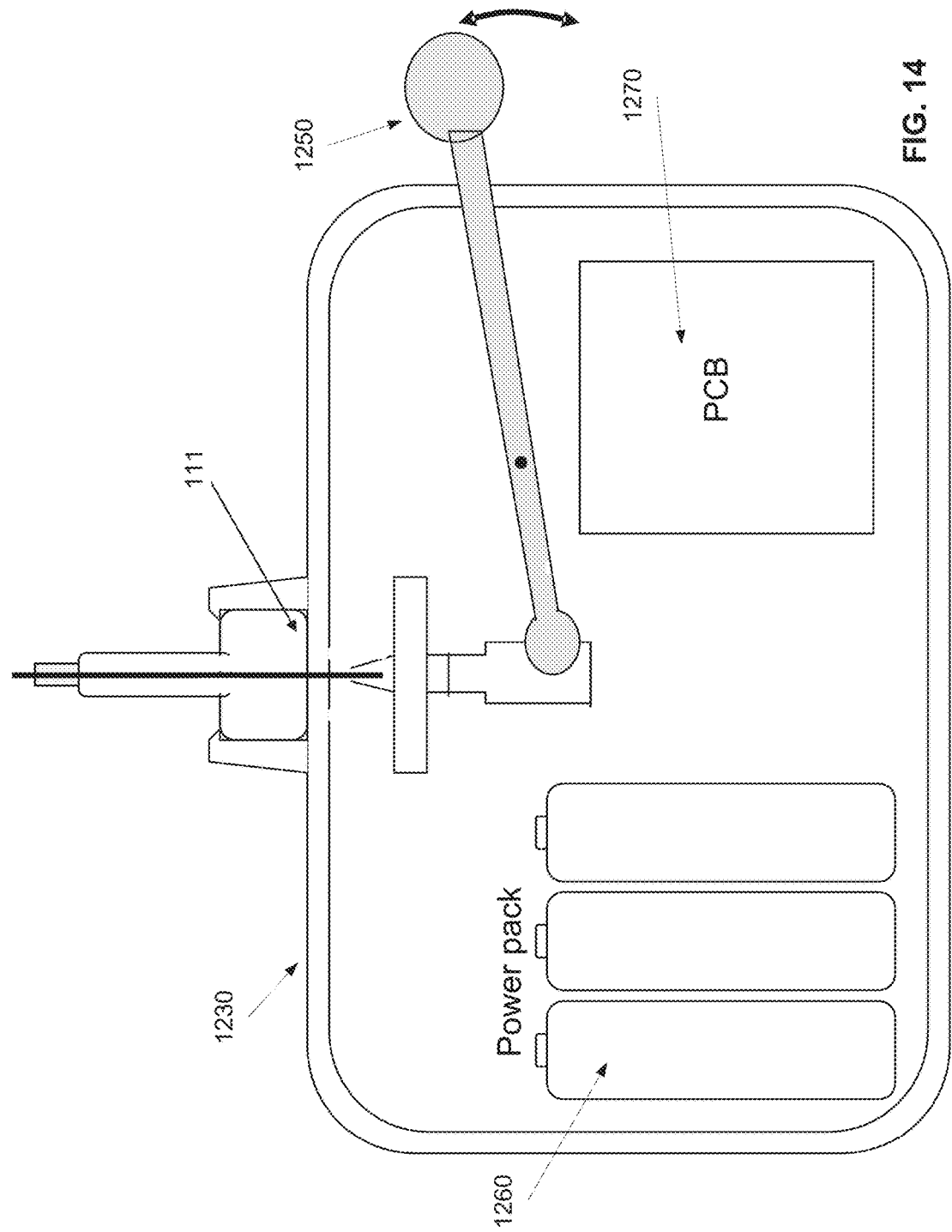

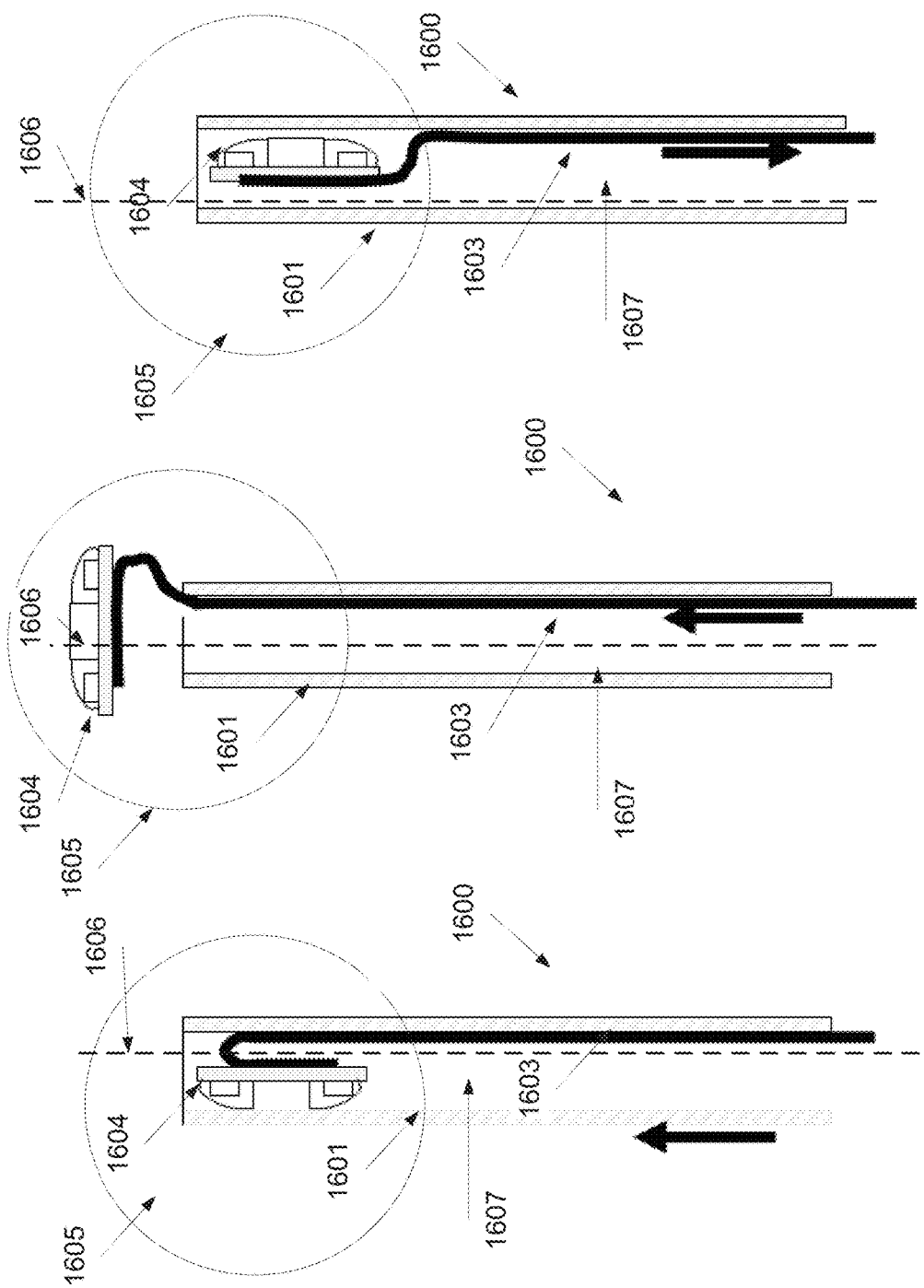

POSTPYLORIC FEEDING DEVICE AND METHODS FOR USING THEREOF

RELATED APPLICATION

This application is claims priority from 61/575,730, filed on 29 Aug. 2011. The content of the above document is incorporated by reference as if fully set forth herein.

FIELD AND BACKGROUND OF THE INVENTION

The present invention, in some embodiments thereof, relates to postpyloric feeding and, more particularly, but not exclusively, to in vivo guidance of a feeding tube for postpyloric feeding.

According to both European and American guidelines for enteral and parenteral nutrition, enteral feeding is the preferred method of nutritional support in patients who have a functioning gastrointestinal (GI) tract but cannot maintain an adequate oral intake. Enteral nutrition prevents GI mucosal atrophy, keeps intestinal integrity and prevents bacterial translocation from the GI lumen to the rest of the body, by maintaining normal permeability of the GI mucosal barrier. In addition, it is less expensive and has fewer complications than parenteral nutrition. The enteral route traditionally delivered nutrition directly into the stomach via a nasogastric tube or gastrostomy (prepyloric feeding).

Over the past few decades, postpyloric feeding has been developed and adopted by nutritional teams for enteral feeding. The indications for this kind of feeding are increasing and include a variety of clinical conditions, such as gastroparesis, acute pancreatitis, gastric outlet stenosis, hyperemesis (including gravida), recurrent aspiration, tracheoesophageal fistula and stenosis in gastroenterostomy. A wide variety of postpyloric nutrition devices are currently available, including different types of nasoduodenal and nasojejunal tubes and jejunostomies, see Eva Niv, at. el. Post-pyloric feeding, World J Gastroenterol. 2009 Mar. 21; 15(11): 1281-1288, Published online 2009 Mar. 21. doi: 10.3748/wjg.15.1281.

SUMMARY OF THE INVENTION

According to some embodiments of the present invention, there is provided a feeding tube device for postpyloric feeding. The device comprises a bendable feeding tube having a proximal end, a central portion and, and a distal end and a delivery lumen therealong for conducting a digestible substance therethrough, the bendable feeding tube being sized and shaped for being disposed within the esophagus so that at least the distal end passes the esophagus sphincter of a patient, an imaging unit having an image sensor mounted on a tip of the distal end to image an imaging space thereinfront, and a tilting mechanism for tilting the distal end in relation to the central portion. The distal end has at least one lateral tilt and feeding opening therealong for delivering the digestible substance therethrough, the at least one lateral tilt and feeding opening are laid out so that when the tilting mechanism tilts the distal end the at least one lateral tilt and feeding opening narrows.

According to some embodiments of the present invention, there is provided a method of placing a feeding tube device in a patient for postpyloric feeding. The method comprises selecting a bendable feeding tube having a proximal end, a central portion and, and a distal end and a delivery lumen and a guidewire lumen therealong and an image sensor mounted on a distal end tip of the distal end to image an imaging space thereinfront, advancing the bendable feeding tube through the nasal or oral canal and down the esophagus of the patient until at least the distal end passes the esophagus sphincter of the patient, tilting the distal end in relation to the central portion, guiding a guidewire tip of the guidewire via the guidewire lumen and into the pylorus of the patient according to the image, and pushing the bendable feeding tube over the guidewire via the pylorus of the patient.

According to some embodiments of the present invention, there is provided a feeding tube device for postpyloric feeding. The feeding tube device comprises a bendable feeding tube having a longitudinal axis, a proximal end, a distal end, and a delivery lumen that passes a digestible substance therethrough for a delivery via a delivery opening at the distal end and an imaging unit having a rod extending from the proximal end to the distal end of the bendable feeding tube and mechanically connected to an image sensor that is mounted at a tip portion of the rod. The tip portion having a folded configuration wherein the image sensor is parallel to the longitudinal axis and an image capturing configuration wherein the image sensor is perpendicular to the longitudinal axis, wherein the tip portion automatically switches from the folded configuration to the image capturing configuration when the rod is pushed to push the tip portion from the delivery lumen to a space in front of the delivery opening.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 2B-2D depict exemplary distal ends and exemplary components of the image sensor(s), according to some embodiments of the present invention;

FIGS. 2E-2G are respectively a three dimensional schematic illustration, a front illustration, and a side illustration of the tip of the distal end, according to some embodiments of the present invention;

FIGS. 2H-2I depict exemplary distal ends having a port for conducting a tool, according to some embodiments of the present invention;

FIGS. 6B-6F are three dimensional schematic illustrations of an exemplary helical ridge portion, a matching nut, and a return spring from different angles, with an without a segment of the feeding tube, according to some embodiments of the present invention;

FIGS. 8A and 8B are exemplary schematic illustrations of an exemplary feeding tube device, optionally for postpyloric feeding, that has a bendable feeding tube encircled in an electroactive polymers (EAP) tube set to bend when energized with an electric potential, according to some embodiments of the present invention;

FIGS. 12A-12F are schematic illustrations depicting a bendable feeding tube of a feeding tube device which is disposed in the body of a patient so that the central portion are within the esophagus and the distal end thereof in the stomach of the patient, according to some embodiments of the present invention;

FIGS. 13 and 14 respectively and schematically illustrate an exemplary control box 1230 that includes a display 1240 and components of the control box 1230, according to some embodiments of the present invention;

FIGS. 16A-16C are schematic illustrations of a distal tip of a bendable feeding tube of a feeding tube device having an imaging unit for feeding, according to some embodiments of the present invention.

DESCRIPTION OF EMBODIMENTS OF THE INVENTION

The present invention, in some embodiments thereof, relates to postpyloric feeding and, more particularly, but not exclusively, to in vivo guidance of a feeding tube for postpyloric feeding.

According to some embodiments of the present invention, there are provided feeding tube devices, and methods of using thereof, for postpyloric feeding. The methods and systems are based on a bendable feeding tube that supports an image sensor at its tip and incorporates one or more lateral openings which are set and placed to support both delivery of digestible substance and tilting of a distal end of the bendable feeding tube in relation to a central portion thereof.

According to some embodiments of the present invention, the methods and feeding tube devices are based on a bendable feeding tube that includes one or more layer(s) of electroactive polymers. In use, these layer(s) are energized to tilt the distal end of the bendable feeding tube in relation to the central portion thereof. Optionally, the layer(s) include one or more pairs of electrodes to tilt the bendable feeding tube in one or more degree(s) of freedom.

According to some embodiments of the present invention, the methods and feeding tube devices are based on a bendable feeding tube includes a rotating mechanism that allows rotating the distal end of the bendable feeding tube in relation to the central portion thereof by pulling and/or pushing a rod placed along at least some of a lumen of in bendable feeding tube. The rotating mechanism is optionally based on a swirl joint that supports a groove (e.g. of a nut) which is connected to the rod and a helical ridge element that passes in the groove.

According to some embodiments of the present invention, the methods and feeding tube devices are based on a bendable feeding tube that includes a guidewire which may be used for conducting the bendable feeding tube via the pylorus and/or for tilting the bendable feeding tube in the stomach.

According to some embodiments of the present invention, the methods and feeding tube devices are based on a bendable feeding tube and an image sensor that can be extracted from the front tip of the bendable feeding tube by pushing a rod and optionally be replaced in the lumen of the bendable feeding tube by pulling that rod. The width of the sensor may be wider than the width of the lumen of the bendable feeding tube.

According to some embodiments of the present invention, the methods and feeding tube devices are based on a bendable feeding tube that includes a guidewire which may be used for conducting the bendable feeding tube via the pylorus and/or for tilting the bendable feeding tube in the stomach.

Figure 1:
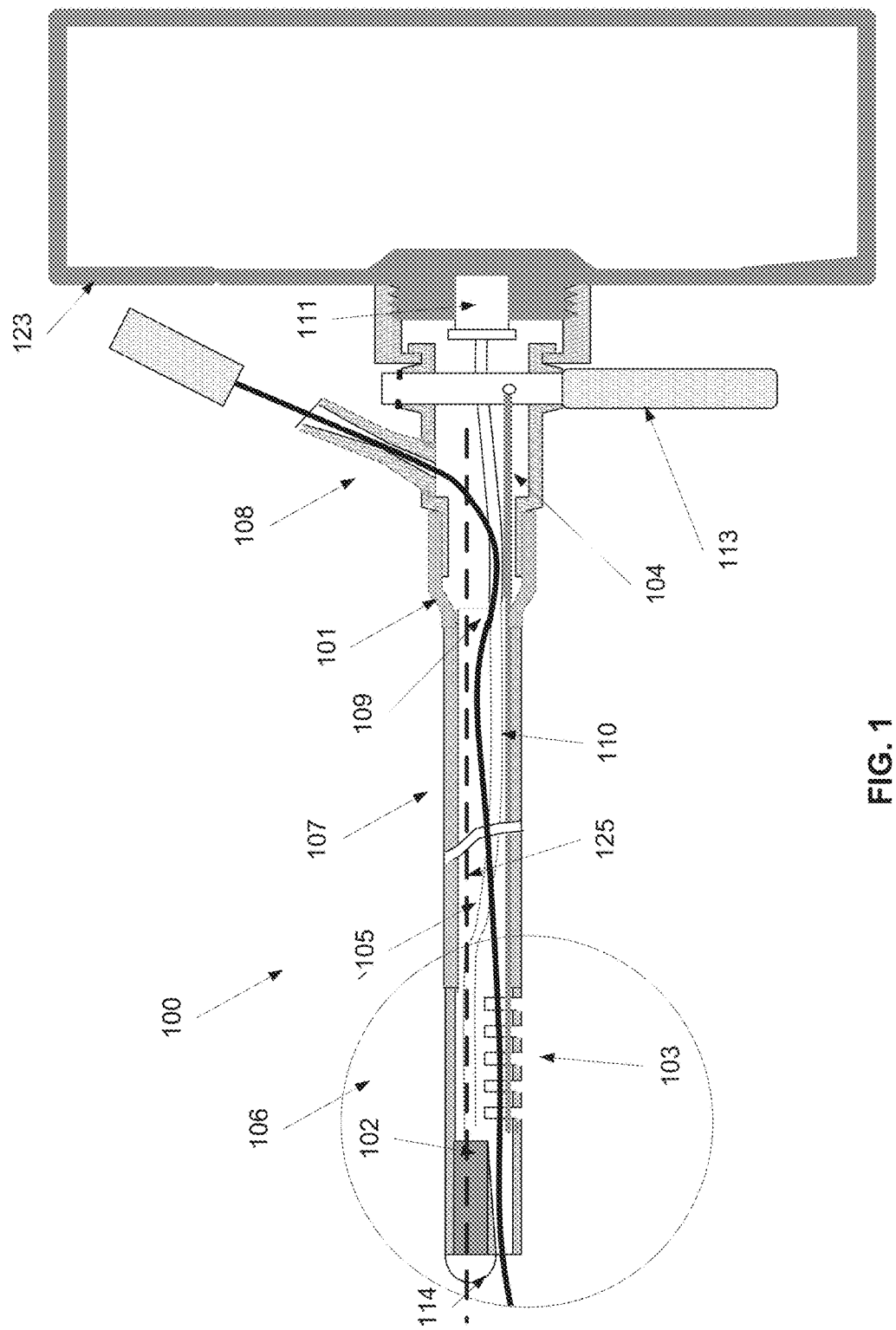
FIG. 1 is a schematic illustration of a feeding tube device for postpyloric feeding having a bendable feeding tube with a delivery lumen for conducting digestible substance for delivery via one or more lateral tilting and feeding openings, according to some embodiments of the present invention.
Figure 2A:
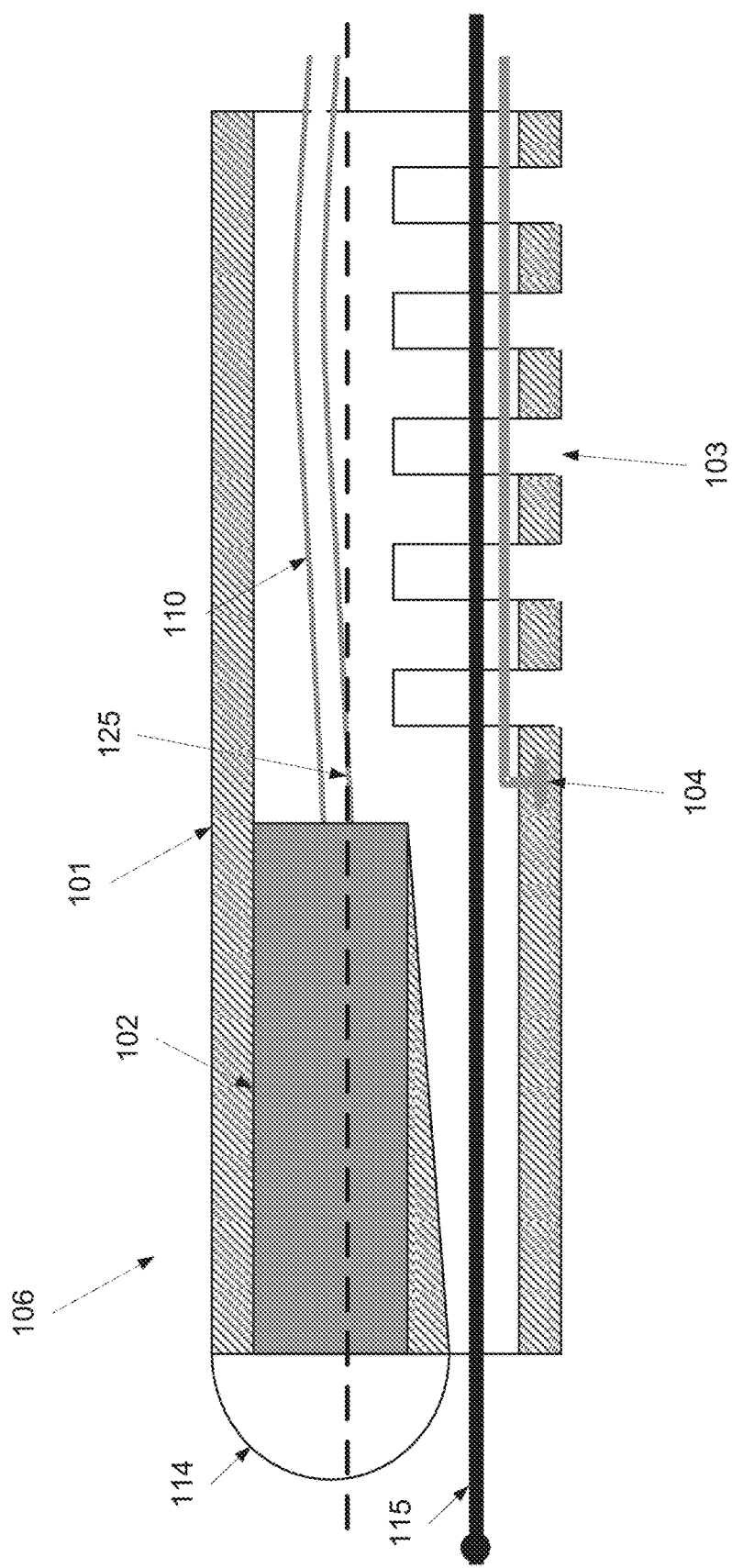
FIGS. 2A and 3 are schematic blow up illustrations of the distal end and the proximal end of the bendable feeding tube depicted in FIG. 1, according to some embodiments of the present invention.
Figure 3:
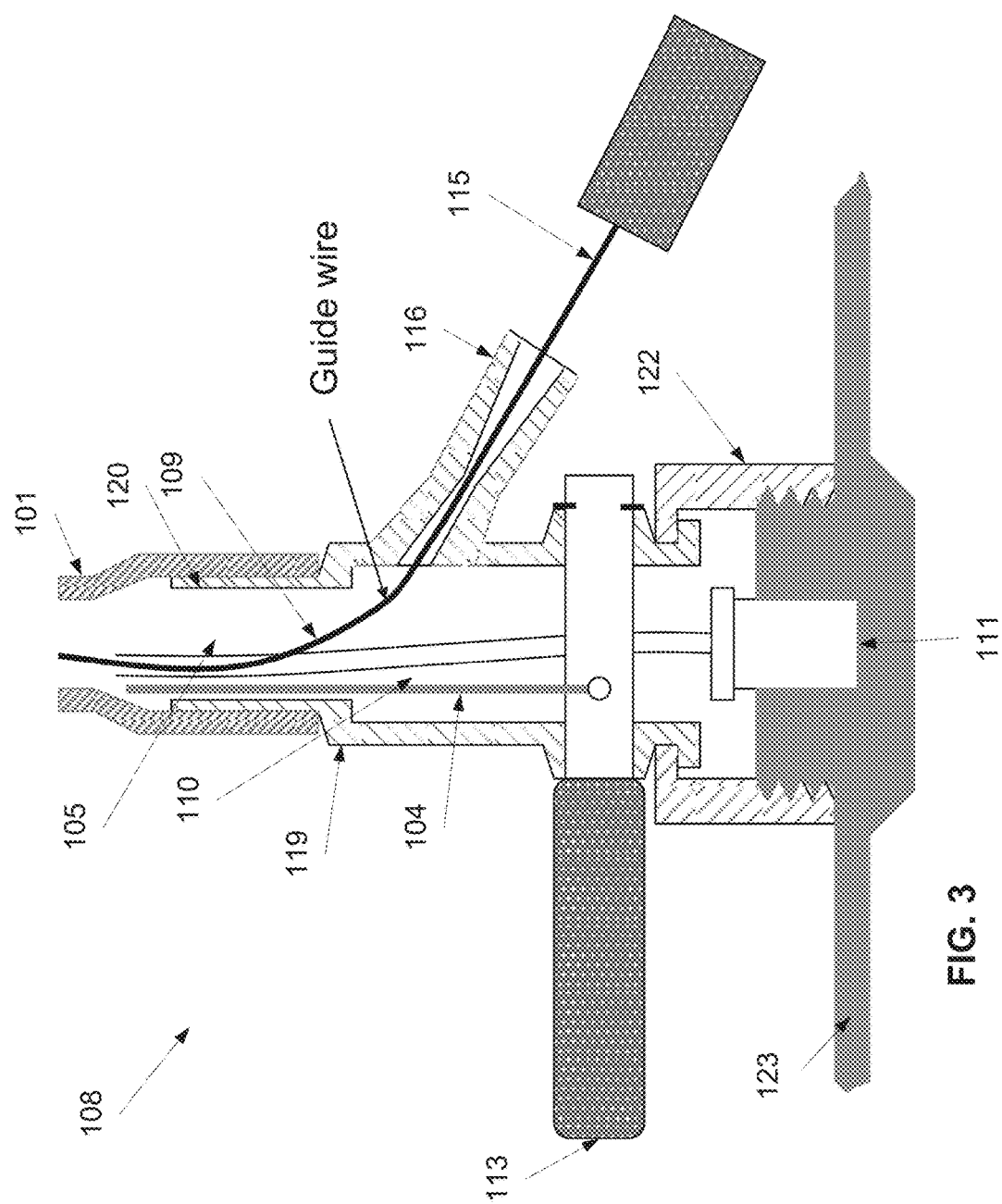

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Reference is now made to FIG. 1, which is a schematic illustration of a feeding tube device 100 for postpyloric feeding having a bendable feeding tube 101 with a delivery lumen 109 for conducting digestible substance, such as nutrients, microorganisms, water and/or medications, for delivery via one or more lateral tilting and feeding openings 103, according to some embodiments of the present invention. The bendable feeding tube 101 is optionally sized for entering the duodenum, for example has an overall diameter of about 3, 4, 5 millimeter (mm) or less. As further described below, the naso/orogastric device 100 may be placed for postpyloric feeding without external imaging, for example X-ray based imaging modalities which are usually used to monitor tube localization. Maneuvering the bendable feeding tube 101 may be done unaided by simple direct manipulation. This assists in reducing costs and cutting a waiting time for performing the procedure. For brevity, the bendable feeding tube 101 is divided to a distal end 106 (marked with a circle), a central portion 107, and a proximal end 108. Reference is also made to FIGS. 2A and 3 which are schematic blow up illustrations of the distal end 106 and the proximal end 108, according to some embodiments of the present invention. The feeding tube device 100 includes an imaging unit with one or more image sensors 102, for example a miniature video camera, and a tilting mechanism 104, 113 for tilting the distal end 106 in relation to the central portion 107, for example to an angle of about 90°, about 75°, about 60°, about 120°, about 105° and/or any intermediate or smaller angle.

The bendable feeding tube 101 is defined herein as any commonly used bendable feeding tube, for example a naso/orogastric feeding tube, a naso-esophageal catheter, a gastric feeding tube, such as a nasogastric feeding tube, a duodenal feeding tube and an enteral feeding tube. The bendable feeding tube 101 is sized and shaped for being disposed within the esophagus so that the distal end 106 is placed in the stomach lumen of a patient. Optionally, the bendable feeding tube 101 comprises a small diameter flexible tube preferably made of transparent plastic, such as polyvinyl Chloride or silicone. The length of the bendable feeding tube 101 is adjusted to the size of the esophagus of the patient. For example, a feeding tube device for adult patients has a bendable feeding tube 101 of more than 120 centimeter long for 18 Fr tube and a feeding tube device for infants has a bendable feeding tube 101 of more than 40 centimeter long for 5 Fr tube.

Figure 2B:
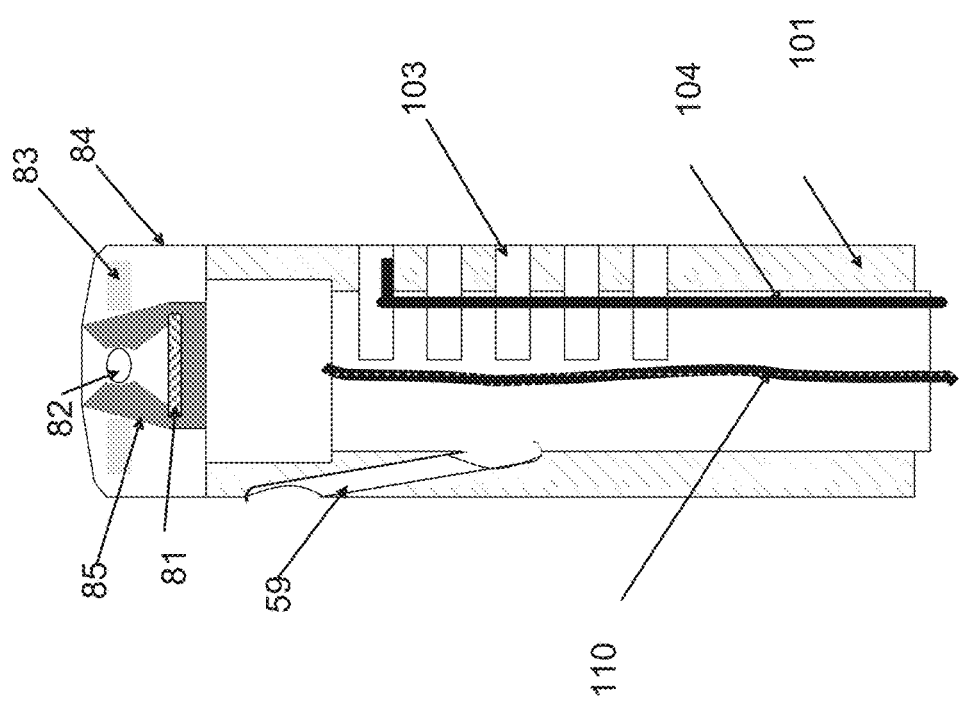
Figure 2C:
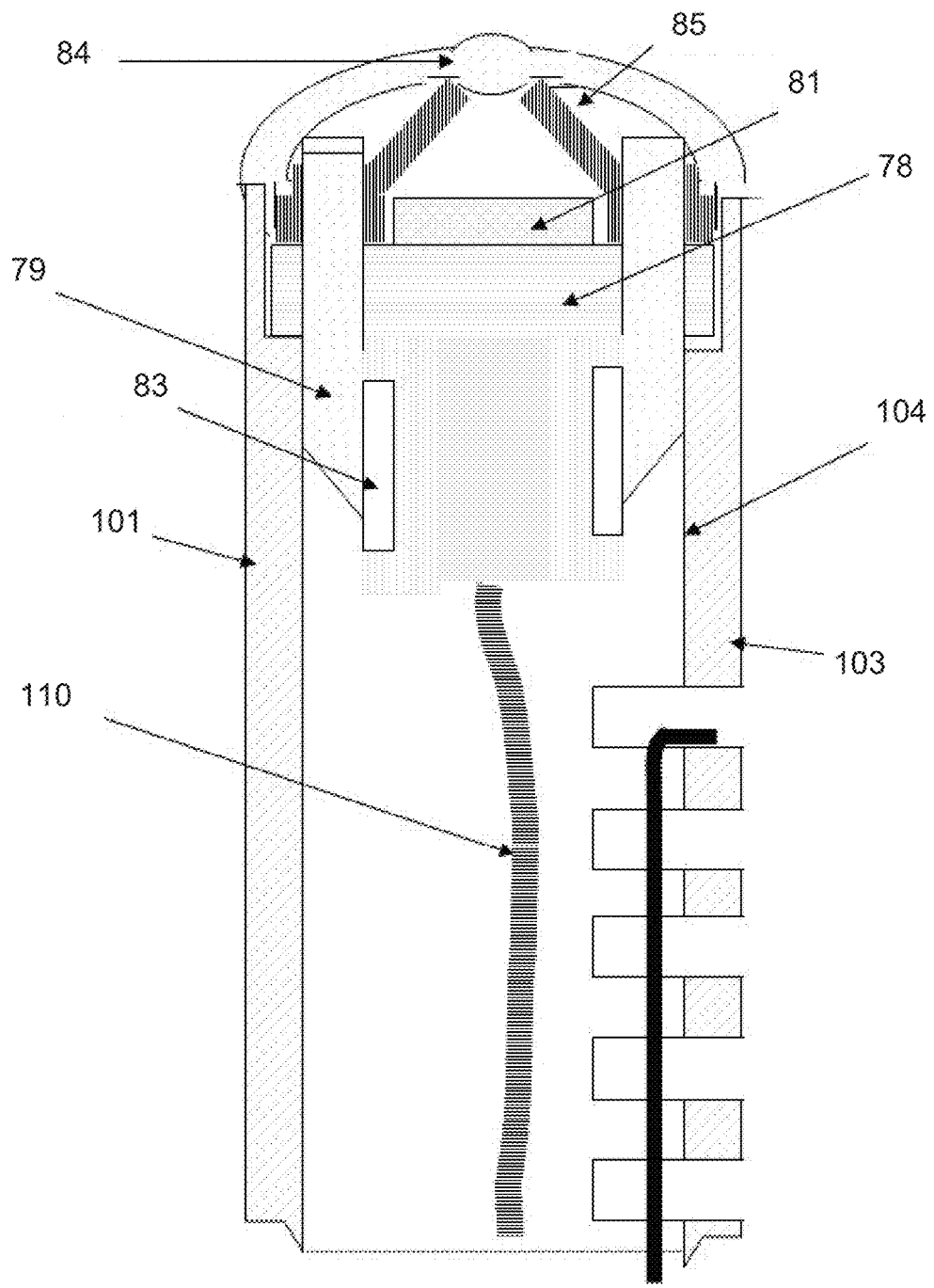

The image sensor(s) 102 of the imaging unit is mounted on the tip 114 of the distal end 106, namely the front tip of the bendable feeding tube 101. This image sensor may block completely the delivery lumen 109, facilitating only a lateral delivery of digestible substance. Alternatively, the image sensor 102 may block part of the delivery lumen 109, facilitating a limited amount of digestible substance to be delivered from the front tip of the bendable feeding tube 101. The diameter of the delivery lumen 109 is optionally about 1 mm, about 2 mm or any intermediate or larger width. The image sensor(s) 102 optionally have dimensions smaller than about 1 mm by about 1 mm. Optionally, the image sensor 102 is equipped with a plastic lens system. For example, the image sensor is a complementary metal-oxide-semiconductor (CMOS) based or charge coupled device (CCD) based sensor. Optionally, the imaging unit includes one or more illumination means for illuminating the space in front of the front tip of the bendable feeding tube 101, for example light emitting diodes (LED) and/or one or more optical fibers which extend between the distal and proximal ends 106, 108. Optionally, the diameter of the image sensor with the LEDs is about 2 mm, compatible with the diameter of the bendable feeding tube 101. For example, FIGS. 2B-2D depict exemplary distal ends and exemplary components of the image sensor(s) 102, according to some embodiments of the present invention. In FIG. 2B, the exemplary components include a CMOS 81, a plastic lens 82, a holder and baffle 85 that support the lens, LEDs 83 and a cover 84. In FIG. 2C, a prism 79 conducts light from the LEDs 83 which are located below the CMOS 81 and optionally a respective printed circuit board (PCB) 79. In FIG. 2D, a fiber optics 69 are used to conduct light from the LEDs 83 which are located below the CMOS 81. Numeral 68 depicts the field of view of the image sensor and numeral 67 depicts the field of illumination of the fiber optics. In this embodiment, the camera is housed in a housing 66.

FIGS. 2E-2G are respectively a three dimensional (3D) schematic illustration, a front illustration, and a side illustration of the tip of the distal end 106, according to some embodiments of the present invention. As shown by numeral 91 and 92, image sensor 91 is mounted to image the space in front of the tip of the distal end 106 and a set of LEDs 91 are mounted to illuminate this space. Optionally, a fluid conducting lumen 93 is set extended in the bendable feeding tube 101, between the proximal and the distal ends 106, 108, to conduct water and/or any other fluid for washing obstacles in front of the image sensor 91. FIG. 2H depicts exemplary distal end having a port 59 for conducting a tool, according to some embodiments of the present invention. The conducted tool may be made from made from super elastic metal pre-formed to a shape that at least the tip of the tool is imaged in the field of view of the image sensor when pushed out from the port 59, for example as shown in FIG. 2I.

The imaging unit optionally includes a communication cable 110, for example a video cable, for forwarding the outputs of the image sensor(s) 102 to an imaging unit, for example a display, such as a liquid crystal display (LCD) display, optionally via a suitable connector 111. The communication cable extends between the distal and proximal ends 106, 108, either in the delivery lumen 109 or in a cable lumen in the body of the bendable feeding tube 101.

Figure 4:
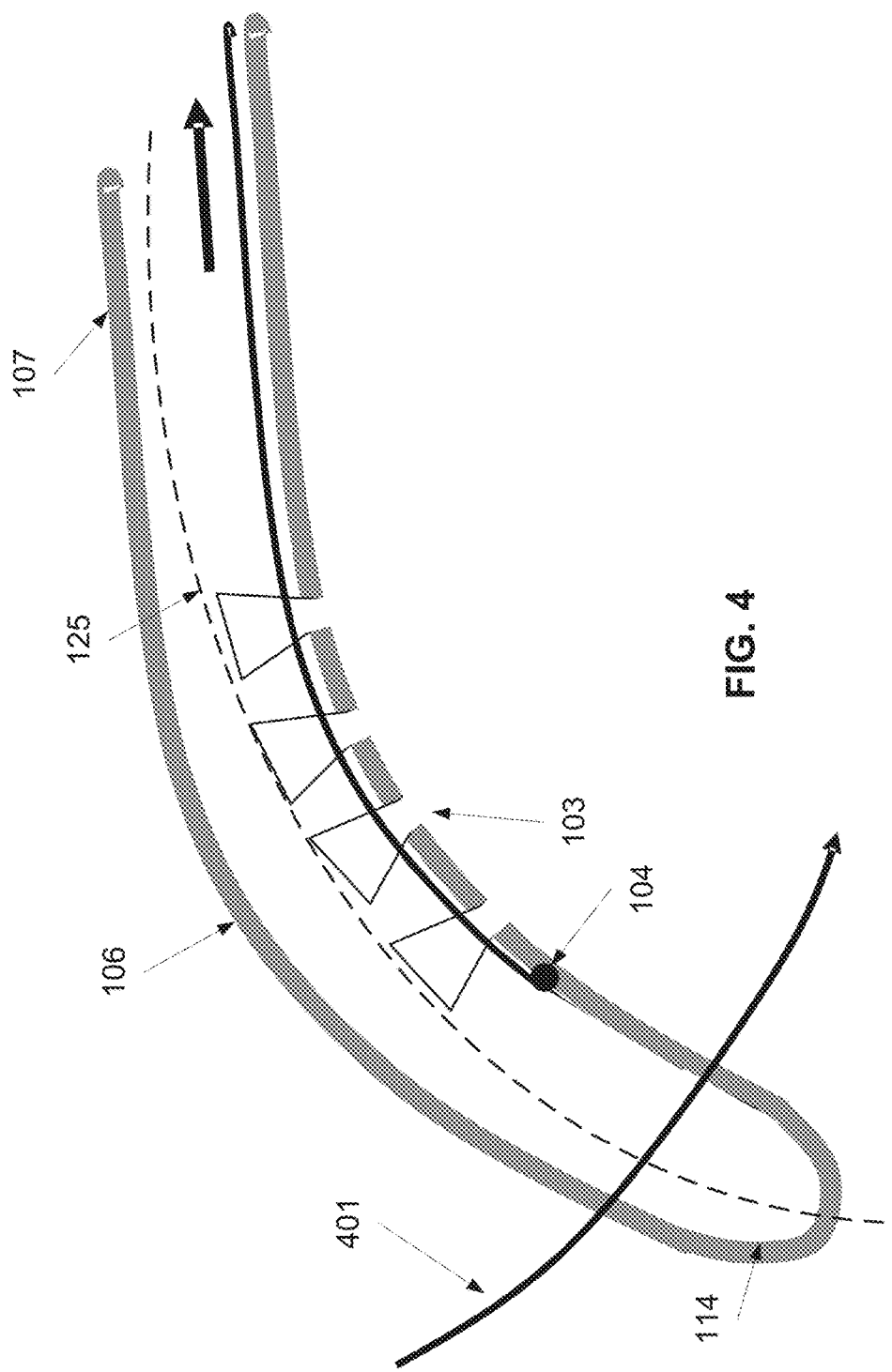
FIG. 4 is a schematic illustration of a tilting of the distal end of the bendable feeding tube in relation to the central portion thereof by lulling a pulling wire that is connected to the distal end, according to some embodiments of the present invention.

The tilting mechanism 104, 113 optionally includes a tilting wire 104 that is mechanically connected to the distal end 106 and a knob 113 for maneuvering the tilting wire 104 so as to tilt the distal end 106 in relation to the central portion 107, for example as described above. As used herein a rod, a wire, a cable, and/or any mechanical element that transmits pulling, pushing, and/or rotating power may be referred to interchangeably. As shown at FIG. 4, the knob 113 optionally pulls the tilting wire 104, inducing the pulling of the distal end 106 toward the proximal end 108, for example as indicated by numeral 401, narrowing the lateral tilting and feeding openings 103 which are located in a portion of the distal end 106. The distal end 106 is arched as an outcome of the pulling. The lateral tilting and feeding openings 103 are lay out in a manner that allows both delivering the digestible substance from the delivery lumen 109 and the tilting of the distal end 106 in relation to the central portion 107, for example in any of the angles described above. During the tilting, as mentioned above and depicted in FIG. 4, the lateral tilt and feeding openings narrow. The portion of the distal end 106 with the lateral tilt and feeding openings has a higher elasticity coefficient than the surrounding portions, for example the central portion 107. This facilitates the bending of the distal end 106 in relation to the central portion 107. The lateral tilt and feeding openings are optionally substantially parallel openings which are elongated perpendicularly to a longitudinal axis 125 of said bendable feeding tube 100.

In use, the user uses the knob 113 to tilt the distal end 106 in a desired angle, optionally while images captured by the image sensor(s) 102 are displayed thereto. In such a manner, the user may direct the front tip of the bendable feeding tube 101 to face the pylorus.

Optionally, the feeding tube device 100 further includes a rotating mechanism for rotating the distal end 106 in relation to the central portion 107, for example as described below. This allows, in use, rotating the tilted distal end 106, for example according to images which are captured by the image sensor(s) 102, until the front tip of the bendable feeding tube 101 to faces the pylorus.

Optionally, a guidewire 115 is extended between the distal and proximal ends 106, 108, either in the delivery lumen 109 or in a guidewire lumen in the body of the bendable feeding tube (for example see numeral 97 in FIGS. 2E and 2F). For brevity, guidewire lumen and delivery lumen are referred to interchangeably herein in this context. The guidewire 115, based on the images which are captured by the image sensor(s) 102, is optionally used for maneuvering the bendable feeding tube 101 via the pylorus, for example as described below. The guidewire 115 is optionally inserted via an opening 116 which may be used as a feeding port for receiving the digestible substance.

Optionally, as depicted in FIG. 3, the proximal end 108 includes a proximal tube holder structure 119 having a protrusion 120 sized and shaped to be fit into the lumen of the bendable feeding tube 101. The opening 116 is optionally formed in the proximal tube holder structure 119. Optionally, a nut 122 connects between the proximal tube holder structure 119 and a control box 123 with a display for presenting the images from the image sensor(s) 102, for example as described below.

According to some embodiments of the present invention, the distal end 106 is tilted using the guidewire. In such an embodiment, the guidewire is shaped to tilt the distal end 106 at an elastic area that has a higher elasticity coefficient, for example at the portion with the lateral tilting and feeding openings 103. For instance, the guidewire elasticity coefficient is lower than the elasticity coefficient of the elastic area and higher than the elasticity coefficient of the central portion 105. Therefore, in a guidewire lumen that extends along the central portion 105, the bended guidewire 115 is straightened and in the distal end 106 the bended guidewire 115 regains its original bending which triggers the tilting of the distal end 106 in relation to the central portion 107, for example to an angle as described above.

According to some embodiments of the present invention, the distal end 106 is tilted one or more shape memory alloy (SMA) wires (not shown) extending at least along a portion of the distal end 106. Each shape memory alloy wire has a straight configuration to allow the conducting of the bendable feeding tube 101 along the esophagus and a bended configuration, wherein the distal end 106 is bended, namely tilted, in relation to the central portion 107. The shape memory alloy wire(s) transfer from a straight configuration to a bended configuration by heating. Optionally, the shape memory alloys are connected to a heating module via the proximal end 108 that is controlled for bending and/or straightening the distal end 106, for instance during the disposing of the feeding tube device 100 for postpyloric feeding and/or the indisposing of the feeding tube device 100 after postpyloric feeding.

Figure 5:
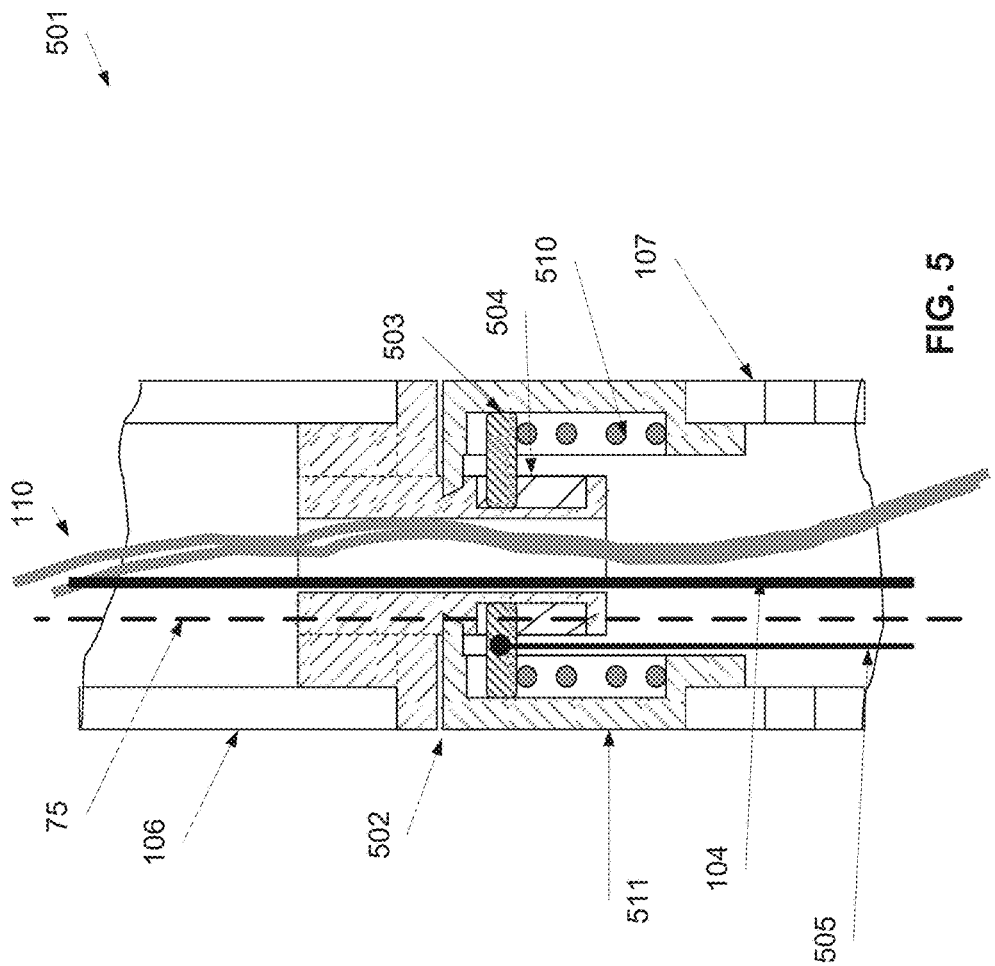
FIG. 5 is a schematic illustration of an exemplary rotating mechanism that is based on a swirl joint, according to some embodiments of the present invention.

Reference is now also made to FIG. 5, which is a schematic illustration of an exemplary rotating mechanism 501 that is based on a swirl joint 502 which connects, in a rotatable manner, between lower and upper parts of the bendable feeding tube 101 the distal end 106 and the central portion 107 and/or between the central portion 107 and the proximal end 108 and/or between bendable feeding tube 101, for example the proximal end 108, and a control box, according to some embodiments of the present invention.

Optionally, when the swirl joint 502 connects between the distal end 106 and the central portion 107, the lumen of the bendable feeding tube 101 in the distal end and the lumen of the bendable feeding tube 101 in the central portion are separated, for example comprised of separated tubes. Alternatively, the lumen of the bendable feeding tube 101 in the distal end and the lumen of the bendable feeding tube 101 in the central portion are connected, for example comprised of a common tube that is set to be twisted when rotated.

Figure 6A:
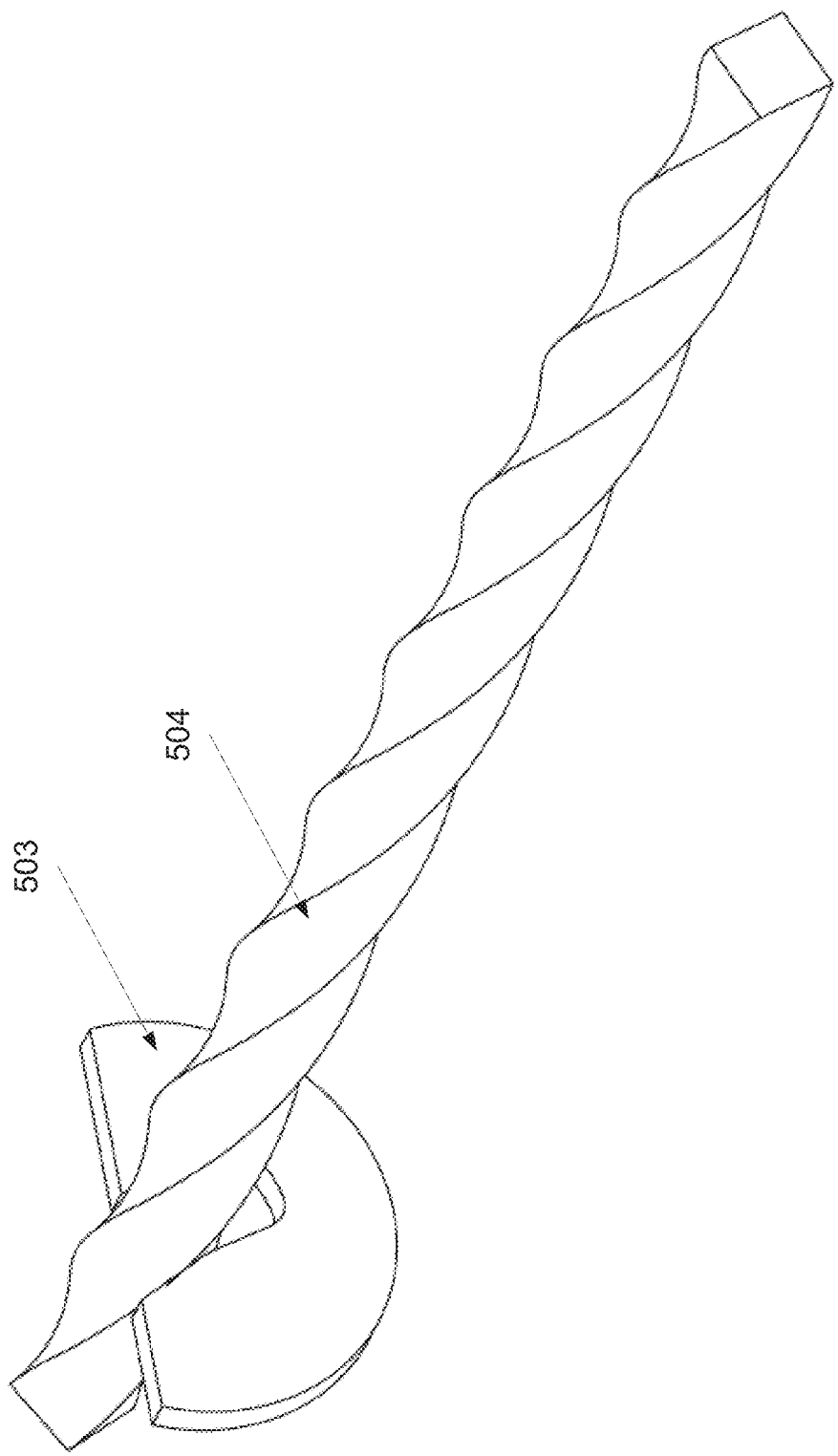
FIG. 6A is a schematic illustration that depicts an exemplary nut and a helical ridge portion of a rod, according to some embodiments of the present invention.

FIG. 5 depicts a number of elements from FIG. 1 and objects which are related to the exemplary rotating mechanism 501. The swirl joint 502 includes a groove, for example in a nut 503, for receiving a helical ridge element 504 that is mechanically connected to the lower part, for example to the distal end 106 or to the bendable feeding tube 101. The nut 503 is connected to a pulling and/or pushing rod 505. Optionally, the helical ridge element 504 has an internal lumen through which the communication cable 110 and optionally the tilt wire 104 are threaded. The nut 503 may be a portion of the rod 505. For example, FIG. 6A is a schematic illustration that depicts an exemplary nut 503 and helical ridge portion 504 of a rod, according to some embodiments of the present invention. When the rod 505 is pulled and/or pushed along the swivel joint 502 the nut 503 rotates the helical ridge portion 504 and together therewith the lower part, for example the distal end 106 or the bendable feeding tube 101 in relation to the central portion 107. The rotation is an outcome of the movement of the helical ridge portion 504 in the groves, for example of the nut 503. Optionally, the nut 503 is placed in a chamber 511 together with a return spring 510 so that the return spring 510 supports the location of the nut 503 in relation to the swivel joint 502, perpendicular to the longitudinal axis of the central portion 75. For example, FIGS. 6B-6F are 3D schematic illustrations of an exemplary helical ridge portion 511, a matching nut 512, and a return spring 513 from different angles, with an without a segment 514 of the feeding tube, according to some embodiments of the present invention.

Figure 6G:
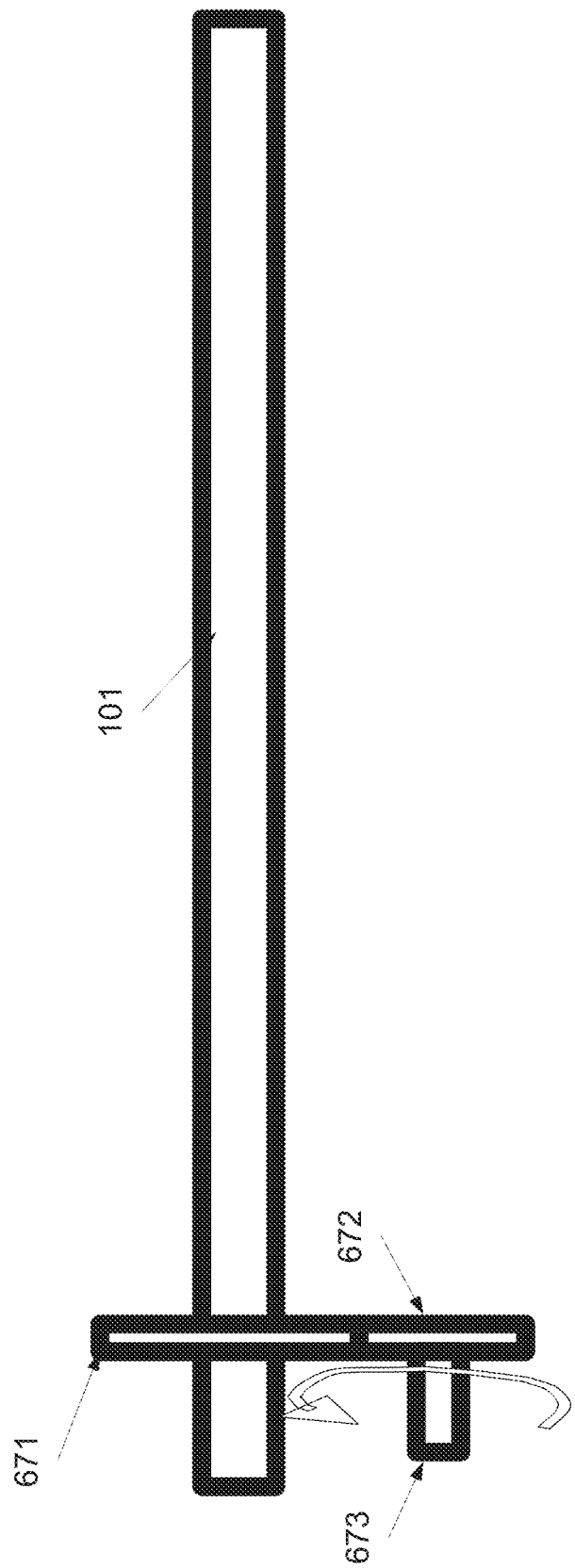
FIG. 6G is a schematic illustration that depicts a mechanism for rotating the bendable feeding tube, according to some embodiments of the present invention.

Reference is now also made to FIG. 6G is a schematic illustration that depicts a mechanism for rotating the bendable feeding tube, according to some embodiments of the present invention. In this embodiment, the rotating mechanism rotates not only the distal end 106 by the bendable feeding tube 101 as a whole. In such embodiments, gearwheel 671 encircles a portion of the bendable feeding tube 101 and another gearwheel 672 is intertwined with gearwheel 671 facilitating the rotating thereof by a control knob 673.

Figure 6H:
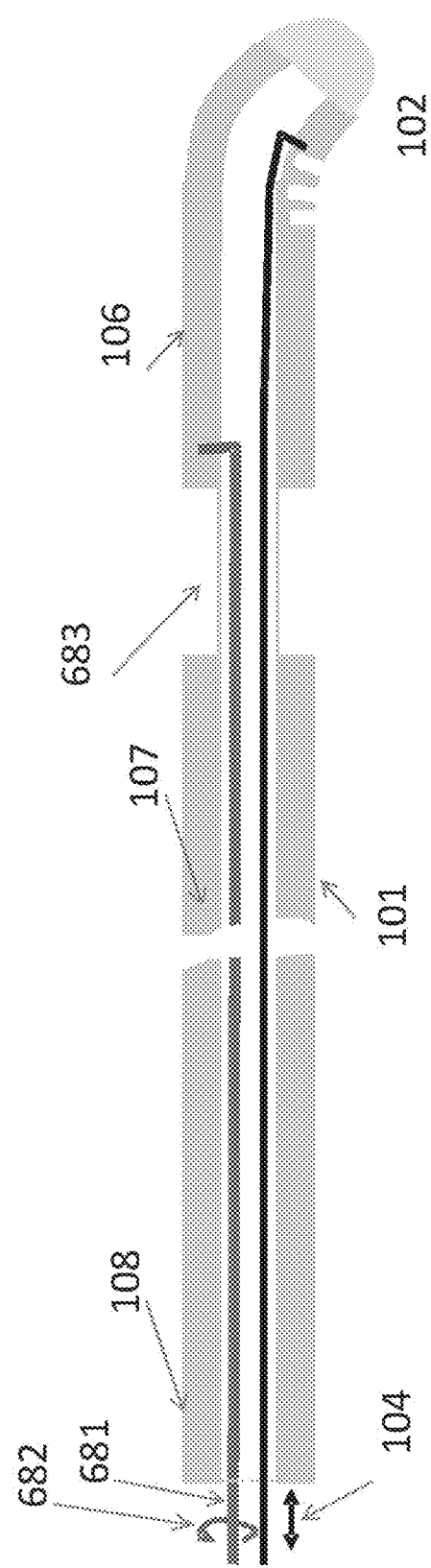
FIG. 6H is a schematic illustration that depicts the bendable feeding tube with a mechanism for rotating the bendable feeding tube that is based on a rotating wire that is mechanically connected to the distal end and optionally not to the central portion through which is passes, according to some embodiments of the present invention.

Reference is now also made to FIG. 6H is a schematic illustration that depicts the bendable feeding tube 101 with a mechanism for rotating the bendable feeding tube 101 that is based on a rotating wire 681 that is mechanically connected to the distal end 106 and optionally not to the central portion 107 through which is passes, according to some embodiments of the present invention. In this embodiment the rotating wire 681 is rotated by a control 682 that is located above the proximal end and mechanically connected thereto. In these embodiments, the rotating mechanism is located externally to the bendable feeding tube 101 and therefore allows maintaining the limited width of the bendable feeding tube 101 itself. Optionally, the area 683 that connects between the distal end 106 and the central portion 107 has a higher elasticity coefficient and therefore ease the rotation of the distal end 106 in relation to the central portion 107. Optionally, the area 683 that connects between the distal end 106 and the central portion 107 includes a rotating joint.

Figure 7:
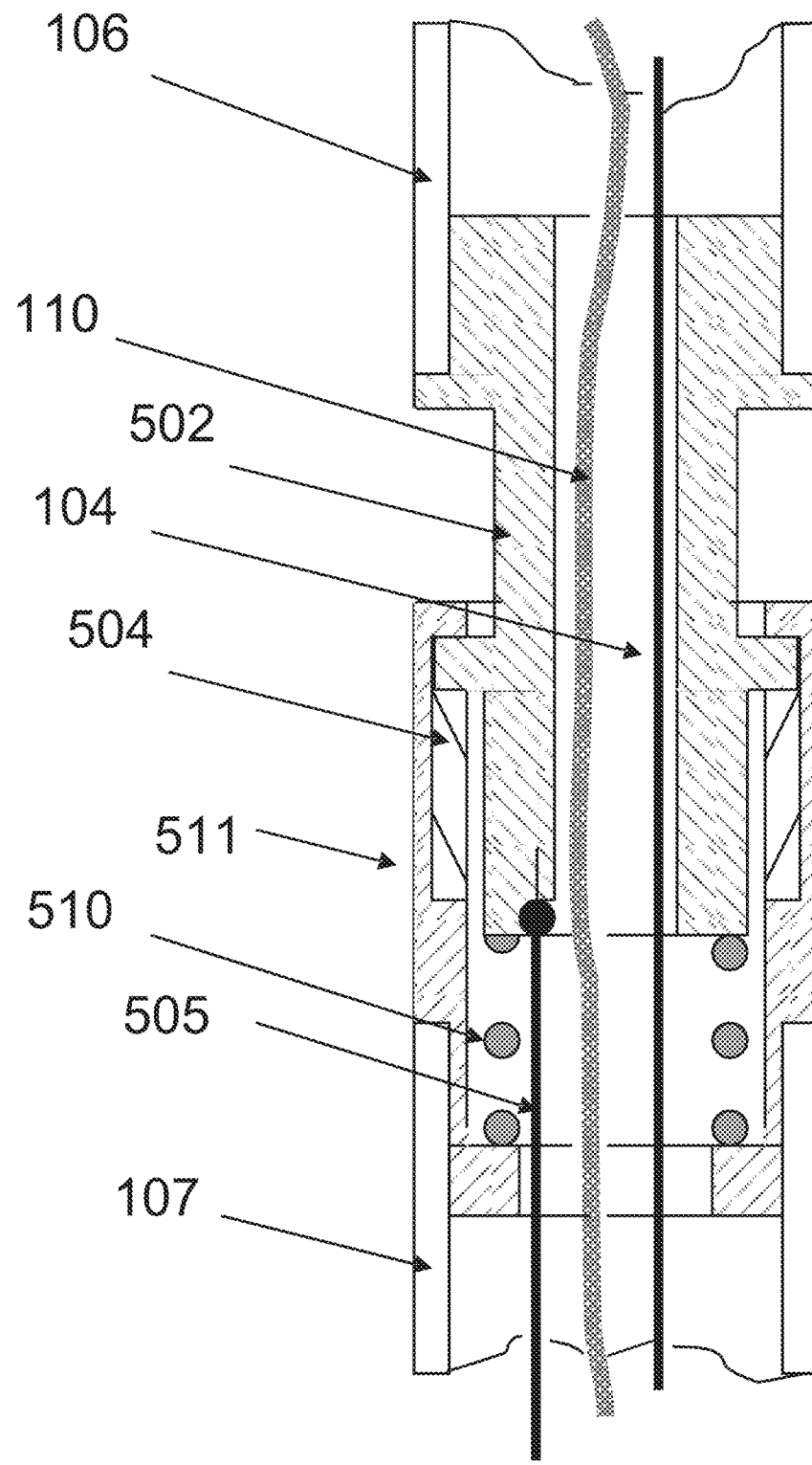
FIG. 7 is a schematic illustration of another exemplary rotating mechanism 701 that is based on an elongated swirl joint, according to some embodiments of the present invention.

Reference is also made to FIG. 7 is a schematic illustration of another exemplary rotating mechanism 701 that is based on an elongated swirl joint 702 which connects, in a rotatable manner, between the lower part and the upper part and/or between the bendable feeding tube 101 and a control box, according to some embodiments of the present invention. FIG. 7 depicts a number of elements from FIG. 5 and objects which are related to the exemplary rotating mechanism 701.

Reference is now made to FIGS. 8A and 8B which are exemplary schematic illustrations of an exemplary feeding tube device 800, optionally for postpyloric feeding, that has a bendable feeding tube 801 with a delivery lumen 809 for conducting digestible substance which is placed in and/or along an electroactive polymers (EAP) tube 810 that bends when energized with an electric potential, according to some embodiments of the present invention. The EAP tube may be a separate tube, a layer on the bendable feeding tube 801 and/or otherwise part of the bendable feeding tube 801. The EAP tube 810 includes an electrical circuit with electrodes 811 which are spread therealong. In use, a control circuit energizes the electrodes 811, which function as transverse deflection electrodes, to induce the bending of the EAP tube 810 to a desired tilt.

Figure 9B:
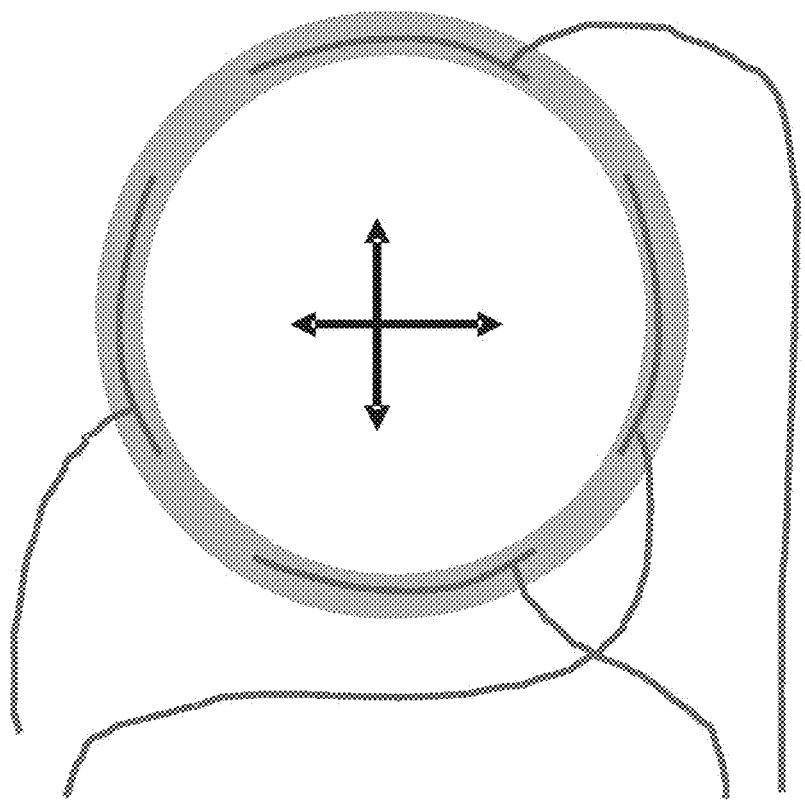
FIGS. 9A and 9B are cross section schematic illustrations respectively depicting two opposite electrodes an two pairs of opposite electrodes which are spread along a bendable feeding tube, according to some embodiments of the present invention.
Figure 9A:
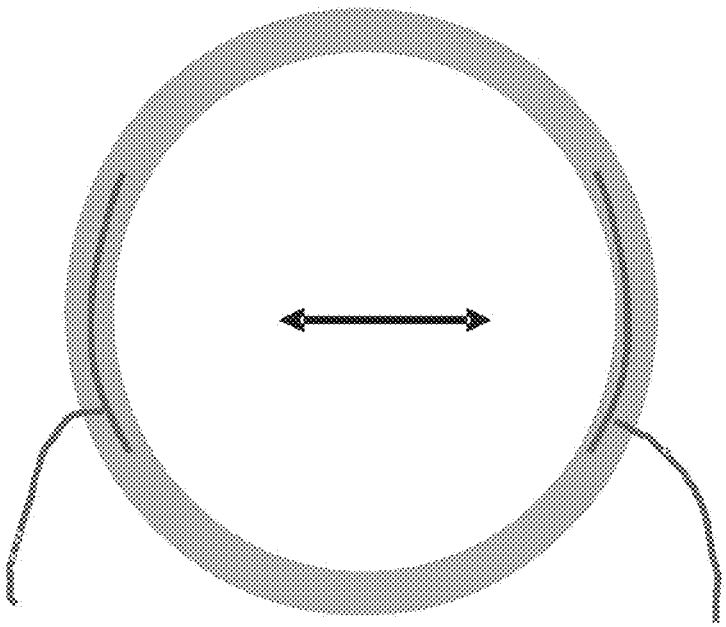

Optionally, as shown at FIG. 9A, two opposite electrodes are spread along the bendable feeding tube 801, facilitating bending a single degree of freedom. Optionally, as shown at FIG. 9B, two pairs of opposite electrodes are spread along the bendable feeding tube 801, facilitating bending in two degrees of freedom. Similarly, it should be noted that different number of pairs of opposite electrodes maybe spread along the bendable feeding tube 801 facilitating bending in various degrees of freedom, for example 3, 5, 10 or any intermediate or larger number.

The EAP tube 810 changes its shape in response to an electrical stimulus, for example as exemplified by the difference between FIG. 8A wherein no electric stimulus is passed via the EAP tube 810 and FIG. 8B wherein electric stimulus is passed via the EAP tube 810. For example, in some embodiments the EAP material may expand about 0.5% to about 20% when exposed to an electric current of 0.001 microAmps to 1 milliAmps (−2 to +2 V). Some examples of materials that may be used for the EAP tube 810 may include polypyrroles, polyanilines, polythiophenes, polyethylenedioxythiophenes, poly(p-phenylenevinylene)s, polysulfones, polyacetylenes, Nafion, Bucky paper and/or any other ionic electro-active polymer that is considered to have low voltage, low speed, high stress (up to 500 MPa), characteristics. Furthermore, it is contemplated that any electroactive polymer that exhibits contractile or expansile properties may be used in connection with the various active regions of the invention, including those listed above. EAP materials and some of their notable characteristics are described in an article entitled ElectroActive Polymer Actuators for Planetary Applications by Y. Bar-Cohen et al. and published in Paper No. 3669-05 of the 40 Proceedings of SPIE Annual International Symposium on Smart Structures and Materials, March 1999, Newport Beach, Calif. SPIE Copyright 1999, the entire contents of which being incorporated herein by reference.

Figure 10A:
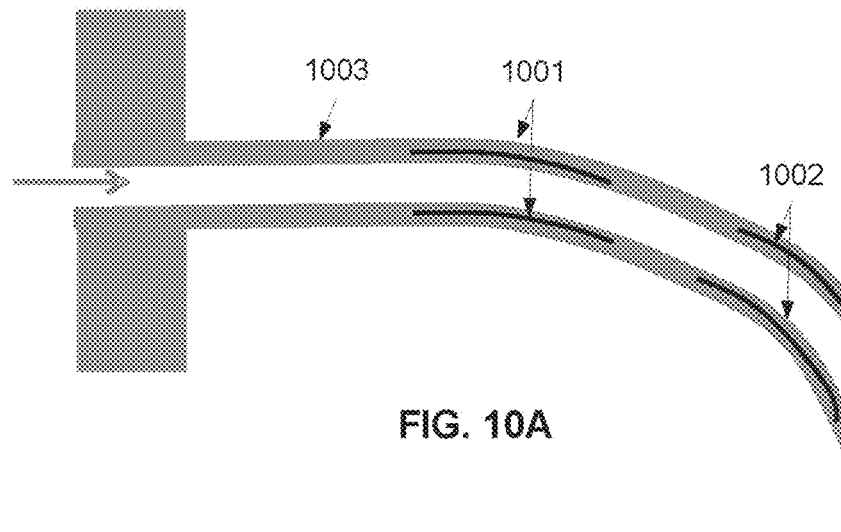
FIGS. 10A and 10B are schematic illustrations depicting a plurality of pairs of electrodes which are located to bend separately a number of different nonoverlapping segments along a bendable feeding tube, according to some embodiments of the present invention.
Figure 10B:
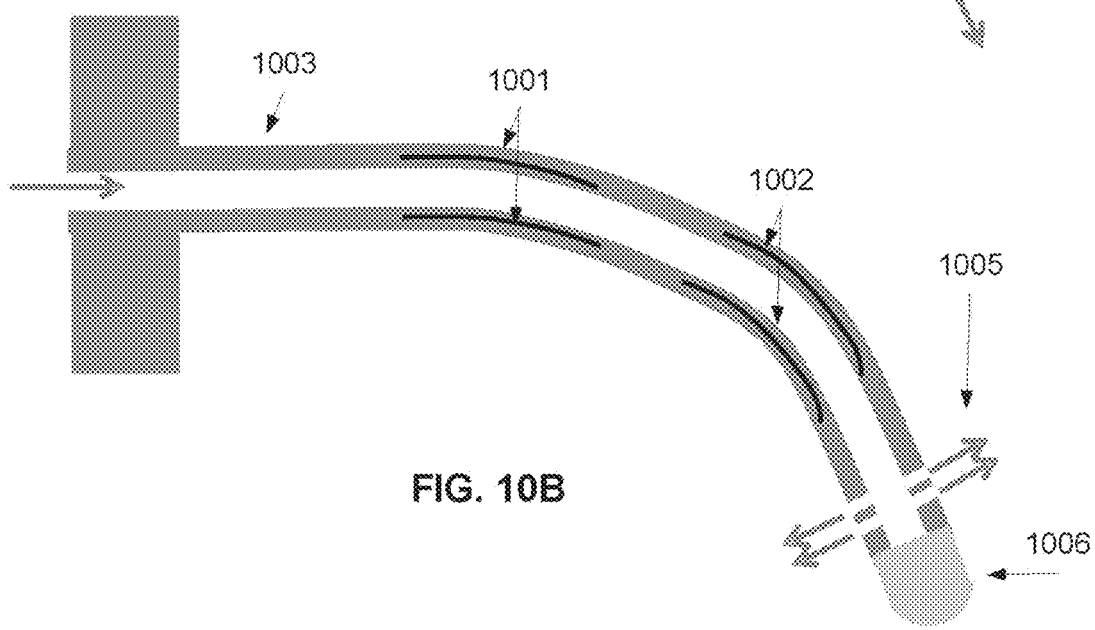

Optionally, as shown at FIG. 10A, a plurality of pairs 1001, 1002 of electrodes are located to bend separately a number of different nonoverlapping segments along the bendable feeding tube 1003, according to some embodiments of the present invention. This allows controlling the bending in a number of degrees of freedom. As shown at FIG. 10B, a camera head may be placed in the front tip of the bendable feeding tube 1003. In such embodiments, digestible substance is delivered via lateral openings 1005, for example similarly to the described above lateral openings.

Figure 11:
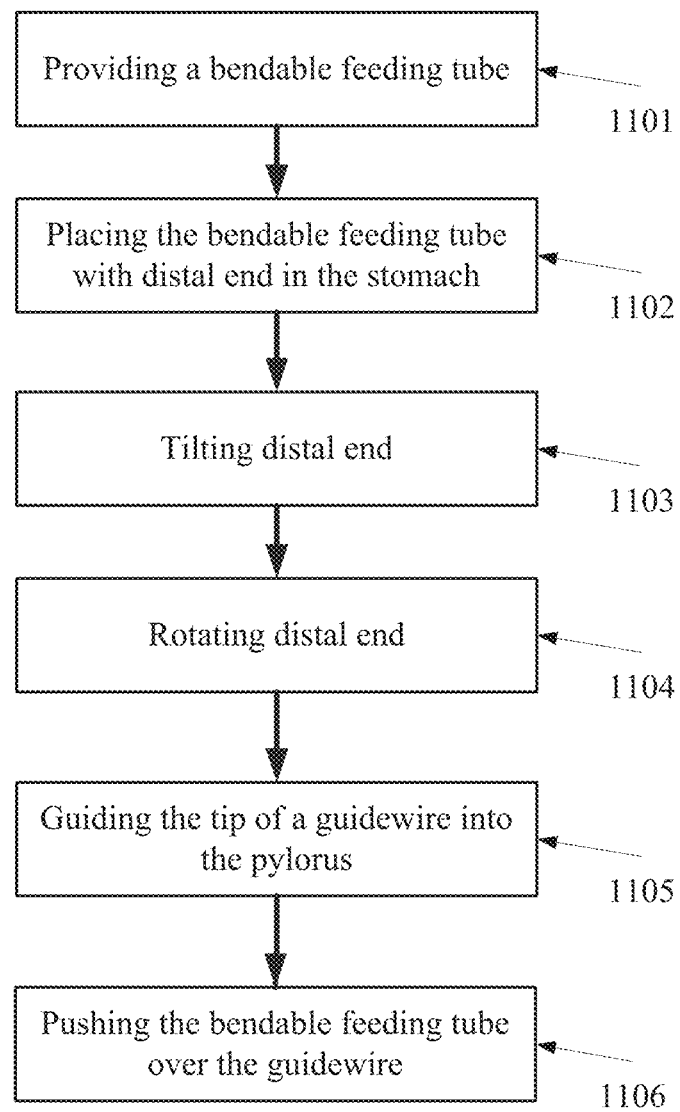
FIG. 11 is a flowchart of a method of placing a feeding tube device, for example as depicted in FIG. 1, for postpyloric feeding, according to some embodiments of the present invention.

Reference is now also made to FIG. 11, which is a flowchart 1100 of a method of placing a feeding tube device, for example as described above, in a patient for postpyloric feeding, according to some embodiments of the present invention. First, as shown at 1101, a device having a bendable feeding tube and an imaging unit, such as bendable feeding tube 101, having bendable feeding tube 801, and/or any of the above described bendable feeding tubes is selected for usage, referred to herein provided. As shown in 1102, the bendable feeding tube is advanced through the nasal or oral canal and down the esophagus of the patient until at least the distal end of the bendable feeding tube passes the Lower esophageal sphincter of the patient and placed in the stomach, for example as shown in FIG. 12A. As shown at FIG. 12B, the image sensor 1120 that is located in the front of the bendable feeding tube is used for imaging the stomach intra space.

Figure 12C:
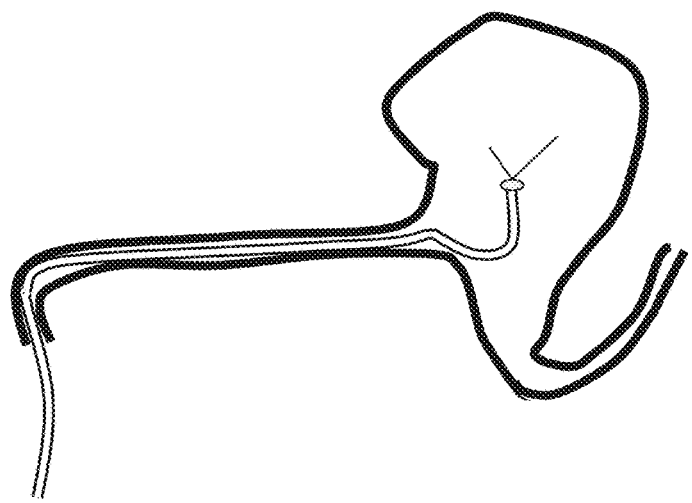
Figure 12B:
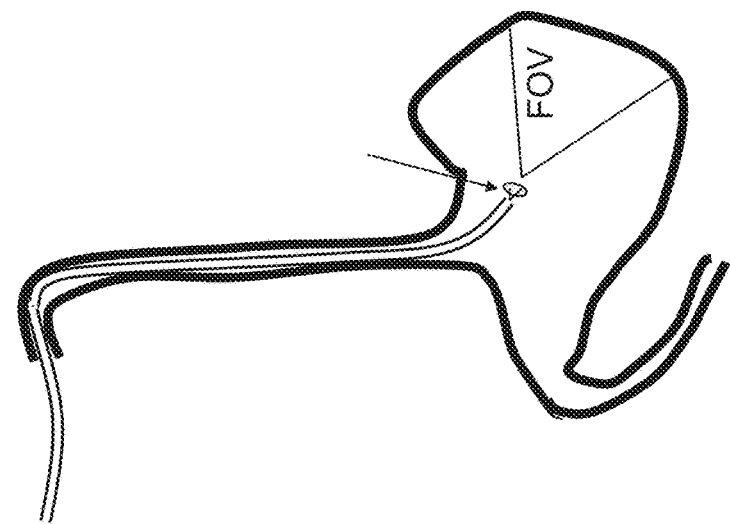
Figure 12A:
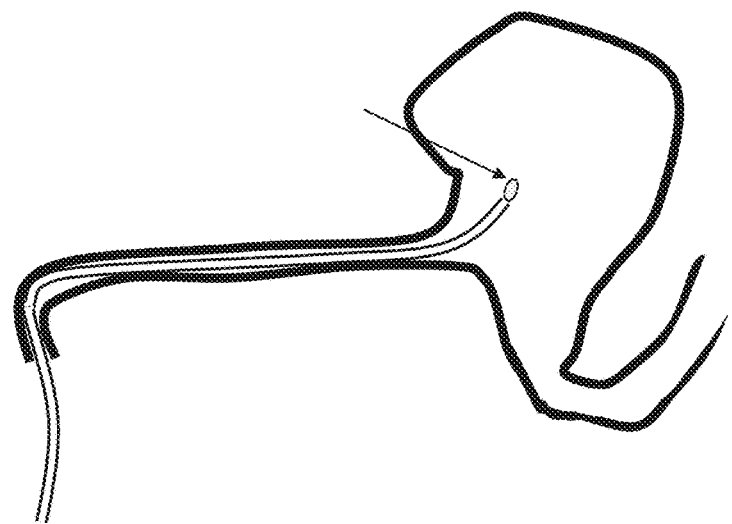
Figure 13:
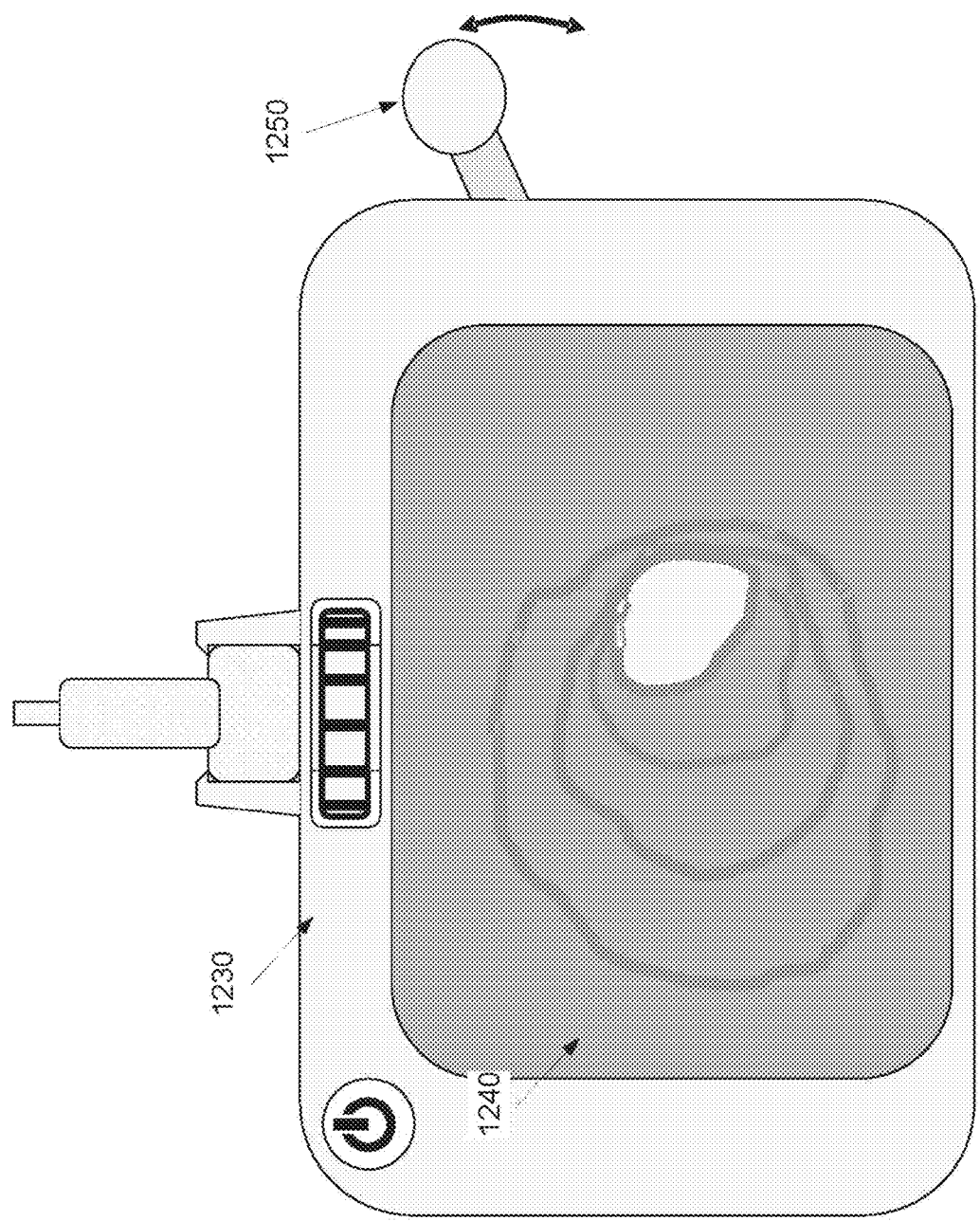

Now, as shown at 1103, the distal end of the bendable feeding tube is tilted in relation to the central portion of the bendable feeding tube, for example as depicted in FIG. 12D, for instance using any of the above described tilting mechanisms. Now, as shown at 1104, the distal end is rotated in relation to the central portion until the front tip of the bendable feeding tube (namely of the distal end) faces the pylorus of the patient. The rotating, and optionally the tilting, are performed according to images from the image sensor. The images are optionally presented in the display of the control box, for example see numeral 123 in FIG. 1. For instance, FIGS. 13 and 14 schematically illustrate an exemplary control box 1230 that includes a display 1240 and components of the control box 1230, according to some embodiments of the present invention. The tilting is optionally performed using user controls, for example using a keypad that activates an EAP layer on the bendable feeding tube. The rotating is optionally performed using user controls, such as knob 1250 which pulls rod 504 (see FIGS. 6A-6F). Now, after the front tip of the bendable feeding tube faces the pylorus, the tilt and rotation orientations of the bendable feeding tube are locked, for example using the control box.

Now, as shown at 1105 and depicted in FIG. 12F, the tip of a guidewire, such as numeral 115 in FIG. 1, is guided into the pylorus of the patient according to the image, for example as shown at 12E. Then, as shown at 1106, the user pushes the bendable feeding tube along and/or over the guidewire via the pylorus of the patient, for example as shown at FIG. 12F. After this process is completed, the control box may be disconnected from the bendable feeding tube and the postpyloric feeding may be initiated. The method depicted in FIG. 11 and the devices depicted in the previous figures allows disposing a bendable feeding tube for postpyloric feeding without using external imaging modalities. The guiding of the bendable feeding tube via the pylorus is done according to images which are acquired by the feeding tube device that is used for the postpyloric feeding itself without using an additional catheter device and/or radiating the patient with imaging radiation.

Optionally, fluid is conducted via a fluid lumen (i.e. see FIGS. 2E-2G) into the imaging space while the images in the imaging space are captured by the image sensor. The fluid allows removing obstacles from the imaging space. Optionally, the fluid includes prokinetic agent that encourages the opening of the pylorus. For example, the prokinetic agent is one of Benzamide, Cisapride, Domperidone, Erythromycin, Itopride, Mosapride, Metoclopramide, Prucalopride, Renzapride, Tegaserod, and Mitemcinal.

Figure 15C:
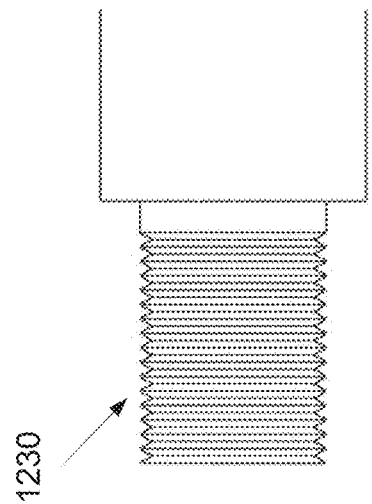
FIGS. 15A-15C are respectively a three dimensional schematic illustration, a front illustration, and a side illustration of the tip of the distal end, according to some embodiments of the present invention.
Figure 15B:
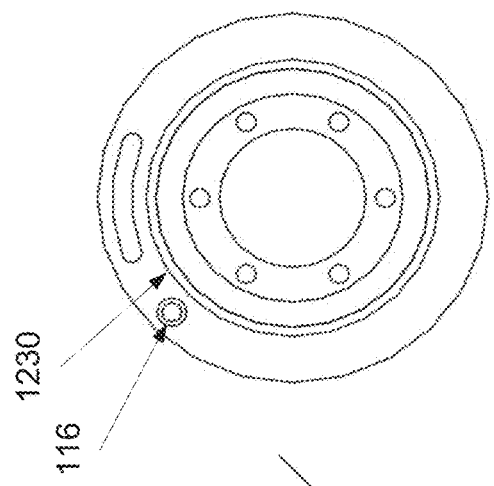
Figure 15A:
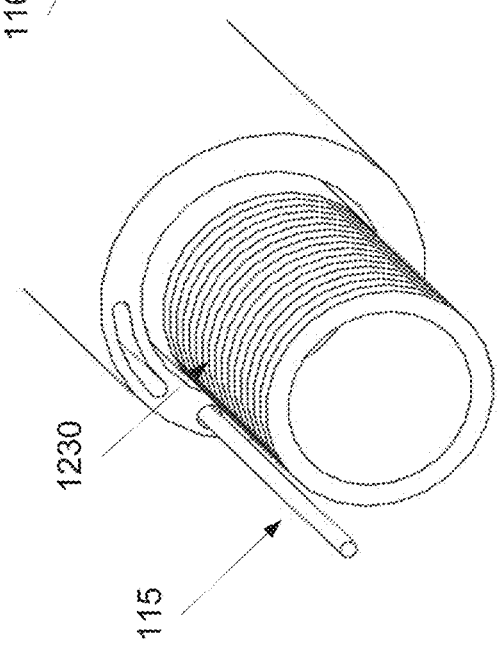

According to some embodiments of the present invention, the distal end has an extension portion, optionally inflatable, that is set to be extended into the pylorus. For example, reference is now made to FIGS. 15A-15C are respectively a 3D schematic illustration, a front illustration, and a side illustration of the tip of the distal end, according to some embodiments of the present invention. The extension portion 1230 is optionally an inflatable bellow. In such an embodiment, a fluid lumen for conducting fluid to inflate the inflatable extension portion 1230 is extended between the proximity end 108 and the distal end of the bendable feeding tube 101. When fluid is conducted therethrough the extension portion 1230 is elongated, for example in about 4, 5, and 6 centimeters or more. This allows extending the bendable feeding tube 101 through the pylorus. This process is optionally guided by the user, for example by an inflation control in the control box. The guidance is provided according to images which are captured by the image sensor, for example as described above. Optionally, fluid is conducted via a fluid lumen (i.e. see FIGS. 2E-2G) into the extension portion 1230 while the images in the imaging space are captured by the image sensor. The fluid may be gas or liquid.

Reference is now made to FIGS. 16A-16C which are schematic illustrations of a distal tip 1600 of a bendable feeding tube 1601 of a feeding tube device having an imaging unit for feeding, for prepyloric or postpyloric feeding, according to some embodiments of the present invention. The feeding tube device may be guided as described above, for example based on images from image sensor 1604, using a tilting and/or rotating mechanisms are described above.

Figure 16D:
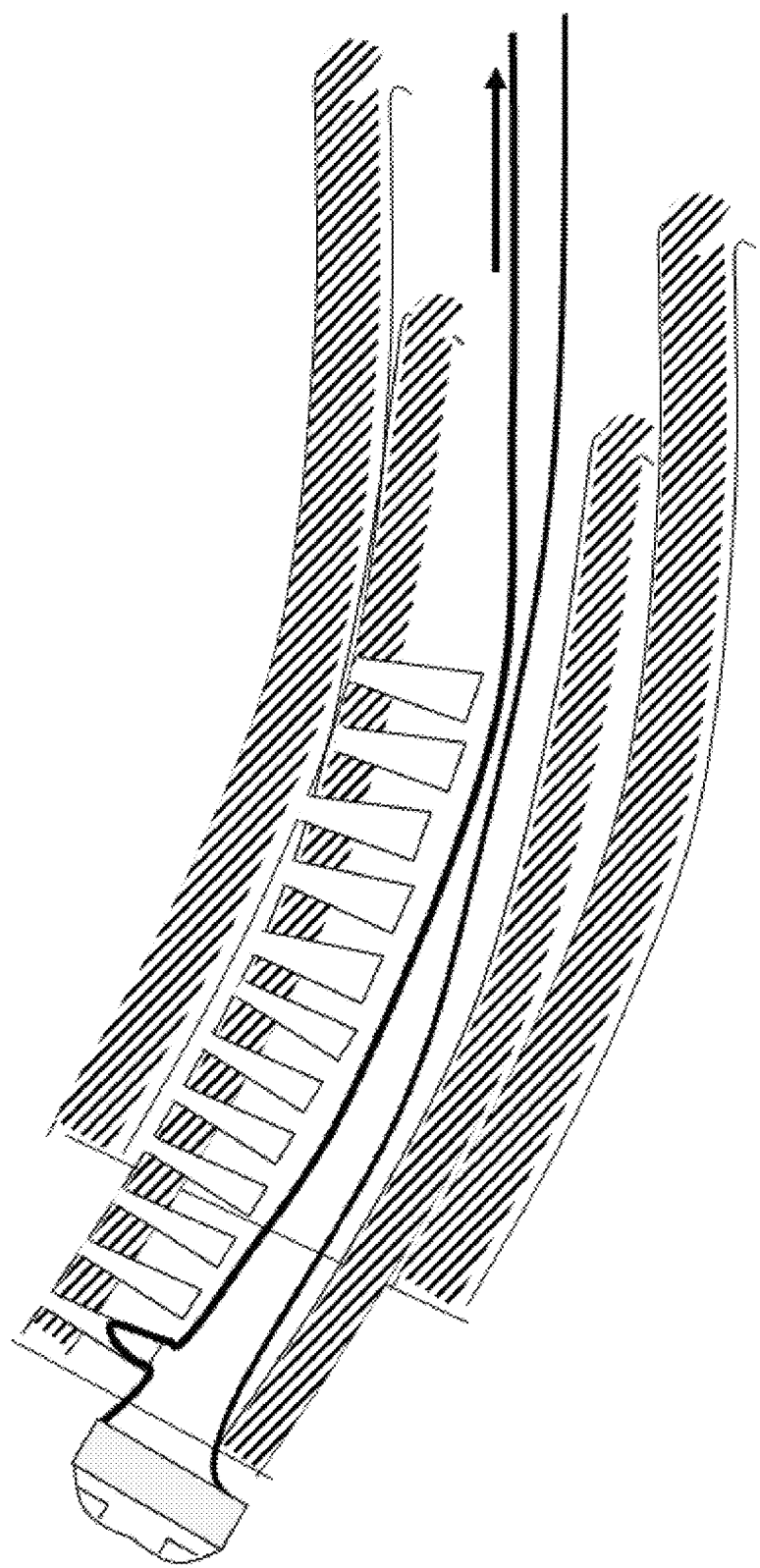
FIG. 16D is a schematic illustration wherein the bendable feeding tube of FIGS. 16A-16C is as described with reference to FIGS. 1-4, according to some embodiments of the present invention.

The bendable feeding tube 1601 is optionally a bendable feeding tube as described above, for example as 101. The feeding tube device includes an imaging unit. The imaging unit includes an image sensor extraction and/or insertion rod 1603 is extended along the bendable feeding tube 1601, from the proximal end to the distal end thereof. The extraction and/or insertion rod 1603 is and mechanically connected to an image sensor 1604 that is mounted at a tip portion 1605 of the rod 1603 The tip portion has a folded configuration, for example as shown in FIG. 16A wherein the image sensor 1604 is parallel to a longitudinal axis 1606 of the distal tip 1600. The tip portion has an image capturing configuration, for example as shown in FIG. 16B wherein the image sensor 1604 is perpendicular to the longitudinal axis 1606. The tip 1605 is optionally made of a shape memory alloy (SMA), for example Nickel titanium (Ni—Ti) so that it automatically switches from the folded configuration to the image capturing configuration when the tip 1605 is pushed from a lumen 1607 of the bendable feeding tube 1601 to a space in front of the opening of the lumen 1607, for example as shown in FIG. 16B. This allows using image sensors which are wider than the width of the lumen 1607. Optionally, the tip 1605 has another folded configuration wherein the image sensor 1604 is parallel to the longitudinal axis 1606, for example as shown in FIG. 16C. The tip 1605 automatically switches from the image capturing configuration to the additional folded configuration when the tip 1605 is pulled into the lumen 1607. In such a manner, the image sensor may be inserted back into the lumen after the guidance process ended. As shown in FIG. 16D, the bendable feeding tube 1601 may be as described above with reference to FIGS. 1-4.

It is expected that during the life of a patent maturing from this application many relevant methods and systems will be developed and the scope of the term a module, an image sensor, a display, and a control is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A feeding tube device for postpyloric feeding, comprising:
    a bendable feeding tube with a delivery lumen for conducting a digestible substance, said bendable feeding tube having a distal end, and a proximal end, said bendable feeding tube comprises:
    a tilting wire passing along said bendable feeding tube, and at least one image sensor mounted on a front tip of the bendable feeding tube;
    a proximal tube holder having:
    a protrusion for connecting a distal end of said proximal tube holder to the proximal end of the bendable feeding tube by fitting into said delivery lumen of said bendable feeding tube, said protrusion is positioned on said distal end of said proximal tube holder, such that said digestible substance is exhausted via said protrusion located within said proximal end of the bendable feeding tube,
    a feeding port sized and shaped for receiving said digestible substance and conducting said digestible substance to said delivery lumen via said protrusion, and
    a knob directly and mechanically connected to said tilting wire for maneuvering said tilting wire so as to tilt the distal end, said knob extending outwardly from a circumferential surface of said proximal tube holder; and
    a communication cable passing through said proximal tube holder and said bendable feeding tube, said communication cable comprises a connector adapted to be connected for forwarding outputs of said the at least one image sensor to a control box when said bendable feeding tube is guided via the pylorus of the patient and disconnected when the patient is fed with said digestible substance.

2. The feeding tube device of claim 1, further comprising a rotating mechanism for rotating said distal end in relation to said central portion.

3. The feeding tube device of claim 2, wherein said rotating mechanism comprises:
    a rotating wire which is mechanically connected to said distal end and passes through said central portion; a rotating control which is external to said bendable feeding tube and rotates said rotating wire along said bendable feeding tube so induce the rotating of said distal end in relation to said central portion.

4. The feeding tube device of claim 1, wherein said bendable feeding tube comprises a plurality of substantially parallel openings each elongated perpendicularly to a longitudinal axis of said bendable feeding tube.

5. The feeding tube device of claim 1, wherein said knob is mounted in said proximal tube holder between said protrusion and said connector.

6. The feeding tube device of claim 1, wherein said tilting wire is a single tilting wire and said distal end is maneuvered only by said single tilting wire.

7. The feeding tube device of claim 1, wherein at least one of said communication cable and said tilting wire is extended along said delivery lumen.

8. The feeding tube device of claim 1, wherein said proximal tube holder further having a nut connected to a proximal end of said proximal tube holder and adapted to mechanically connect to said control box; and
    wherein said communication cable passing through said nut, said proximal tube holder and said bendable feeding tube.

9. The feeding tube device of claim 1, wherein a rotation axis of said knob is perpendicular to a longitudinal axis of said proximal tube holder.

* * * * *